(12) United States Patent
Weselak et al.

(10) Patent No.: US 7,364,907 B2
(45) Date of Patent: Apr. 29, 2008

(54) SYSTEMS AND METHODS FOR SORTING SAMPLES

(75) Inventors: Mark R. Weselak, San Diego, CA (US); Brad Backes, Chicago, IL (US); Jared Ek, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 10/704,335

(22) Filed: Nov. 7, 2003

(65) Prior Publication Data

US 2004/0142486 A1 Jul. 22, 2004

Related U.S. Application Data

(60) Provisional application No. 60/424,898, filed on Nov. 8, 2002.

(51) Int. Cl.
*G01N 35/00* (2006.01)
*B07C 5/00* (2006.01)

(52) U.S. Cl. .................. 436/43; 436/180; 209/522; 422/63; 422/100

(58) Field of Classification Search .............. 422/100, 422/63, 64, 67, 68.1; 436/180, 46, 43; 209/522, 209/523
See application file for complete search history.

(56) References Cited

U.S. PATENT DOCUMENTS

| | | | |
|---|---|---|---|
| 4,118,280 A | 10/1978 | Charles et al. | |
| 4,835,707 A * | 5/1989 | Amano et al. | 700/266 |
| 4,861,553 A * | 8/1989 | Mawhirt et al. | 422/65 |
| 4,861,554 A | 8/1989 | Sakuma | |
| 5,314,825 A | 5/1994 | Weyrauch et al. | |
| 5,363,885 A * | 11/1994 | McConnell et al. | 141/1 |
| 5,439,649 A * | 8/1995 | Tseung et al. | 422/99 |
| 5,479,969 A * | 1/1996 | Hardie et al. | 141/130 |
| 5,544,683 A * | 8/1996 | Guhl | 141/65 |
| 5,681,530 A * | 10/1997 | Kuster et al. | 422/63 |
| 5,769,775 A * | 6/1998 | Quinlan et al. | 494/10 |
| 5,798,035 A * | 8/1998 | Kirk et al. | 205/335 |
| 5,935,859 A * | 8/1999 | Elliott et al. | 436/54 |
| 5,972,295 A * | 10/1999 | Hanawa et al. | 422/65 |
| 6,015,534 A * | 1/2000 | Atwood | 422/102 |
| 6,045,755 A * | 4/2000 | Lebl et al. | 422/65 |
| 6,060,022 A * | 5/2000 | Pang et al. | 422/65 |
| 6,136,274 A * | 10/2000 | Nova et al. | 422/102 |
| 6,156,575 A * | 12/2000 | Fassbind et al. | 436/50 |
| 6,220,451 B1 * | 4/2001 | Hoffmann | 209/522 |
| 6,221,317 B1 * | 4/2001 | Carl | 422/104 |
| 6,225,109 B1 * | 5/2001 | Juncosa et al. | 435/288.5 |
| 6,264,419 B1 * | 7/2001 | Schinzel | 414/751.1 |
| 6,368,872 B1 * | 4/2002 | Juranas | 436/180 |
| 6,383,820 B1 * | 5/2002 | Bunn et al. | 436/518 |
| 6,387,330 B1 * | 5/2002 | Bova et al. | 422/100 |
| 6,413,780 B1 * | 7/2002 | Bach et al. | 436/48 |
| 6,436,349 B1 | 8/2002 | Carey et al. | |

(Continued)

OTHER PUBLICATIONS

Balance Automator® Homepage "Balance Automator" 9 Pages; http://www.bohdan.com/ba.htm.

*Primary Examiner*—Brian R. Gordon
(74) *Attorney, Agent, or Firm*—Timothy L. Smith; Genomics Institute of the Novartis Research Foundation

(57) ABSTRACT

Methods and systems for sorting compounds and compound holders into batches for subsequent processing are provided.

77 Claims, 6 Drawing Sheets

U.S. PATENT DOCUMENTS

Figure 1:
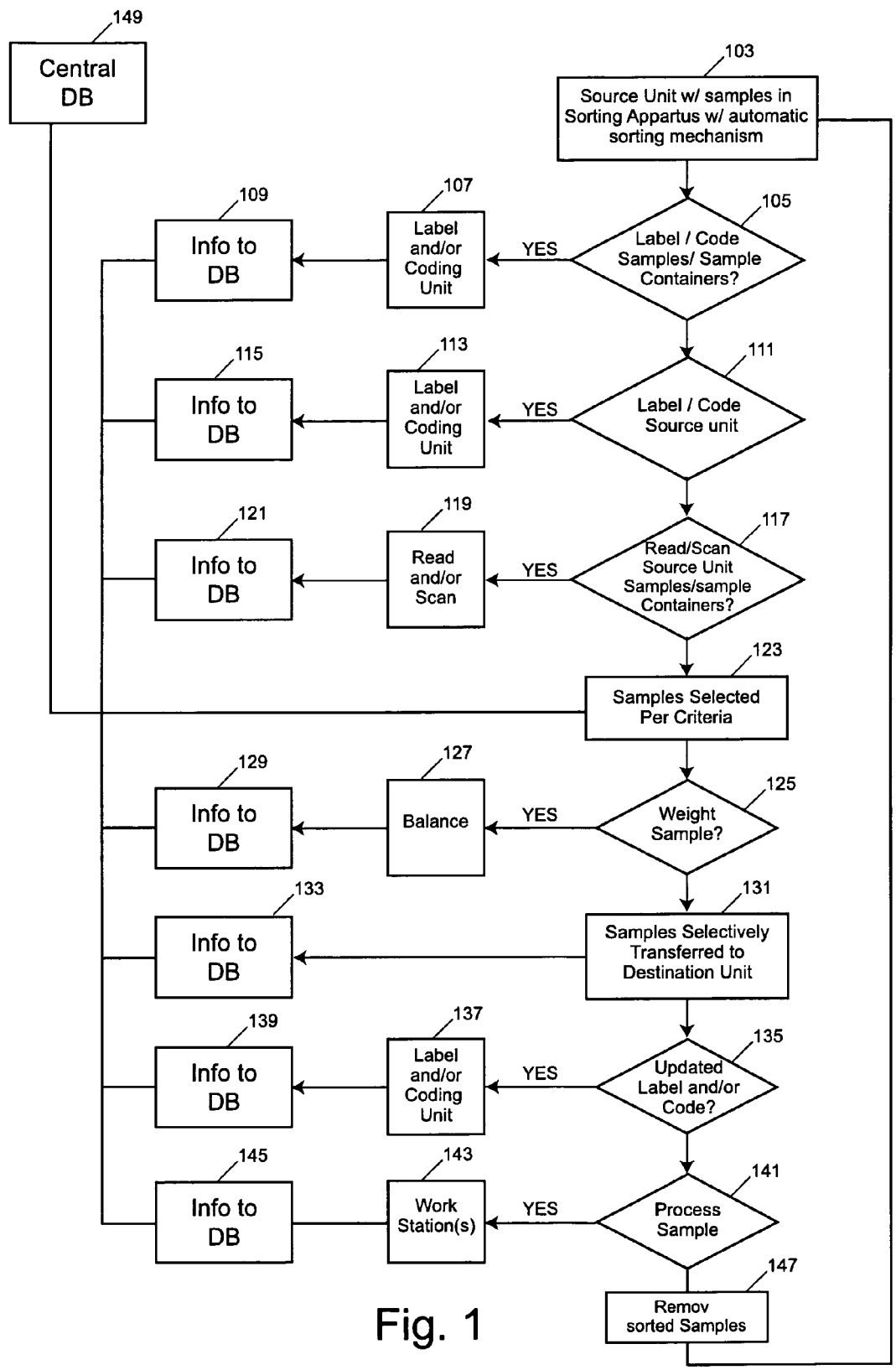

| | | | |
|---|---|---|---|
| 6,451,259 B1 * | 9/2002 | Cohen et al. | 422/63 |
| 6,455,002 B1 * | 9/2002 | Jokes et al. | 422/63 |
| 6,458,324 B1 * | 10/2002 | Schinzel | 422/65 |
| 6,685,884 B2 * | 2/2004 | Stylli et al. | 422/63 |
| 6,720,143 B2 * | 4/2004 | Juncosa et al. | 435/6 |
| 6,761,810 B2 * | 7/2004 | McGrath et al. | 204/459 |
| 6,803,239 B2 * | 10/2004 | Bunn et al. | 436/518 |
| 6,890,485 B1 * | 5/2005 | Stylli et al. | 422/68.1 |
| 6,943,009 B2 * | 9/2005 | Lacey et al. | 435/297.5 |
| 2001/0053337 A1 * | 12/2001 | Doktycz et al. | 422/100 |
| 2002/0001541 A1 * | 1/2002 | Holden et al. | 422/61 |
| 2002/0009391 A1 * | 1/2002 | Marquiss et al. | 422/63 |
| 2002/0012611 A1 * | 1/2002 | Stylli et al. | 422/65 |
| 2002/0021983 A1 * | 2/2002 | Comte et al. | 422/65 |
| 2002/0106305 A1 * | 8/2002 | Willenbring et al. | 422/63 |
| 2002/0119077 A1 * | 8/2002 | Shumate et al. | 422/100 |
| 2002/0127727 A1 * | 9/2002 | Bach et al. | 436/48 |
| 2002/0146832 A1 * | 10/2002 | Michel et al. | 436/43 |
| 2002/0176801 A1 * | 11/2002 | Giebeler et al. | 422/82.05 |
| 2003/0003017 A1 | 1/2003 | Frank et al. | |
| 2003/0017084 A1 | 1/2003 | Dale et al. | |
| 2003/0022380 A1 | 1/2003 | Jakubowicz et al. | |
| 2003/0044990 A1 | 3/2003 | Seto | |
| 2003/0113233 A1 * | 6/2003 | Nanthakumar | 422/100 |
| 2003/0124028 A1 * | 7/2003 | Carlson et al. | 422/68.1 |
| 2004/0002163 A1 * | 1/2004 | Reinhardt et al. | 436/174 |
| 2004/0033168 A1 * | 2/2004 | Hughes et al. | 422/100 |
| 2004/0062688 A1 * | 4/2004 | Guiles et al. | 422/102 |
| 2004/0109791 A1 * | 6/2004 | Itoh | 422/63 |
| 2004/0126283 A1 * | 7/2004 | Backes et al. | 422/104 |
| 2005/0013745 A1 * | 1/2005 | Buchanan et al. | 422/102 |
| 2005/0232822 A1 * | 10/2005 | Reed et al. | 422/100 |

* cited by examiner

SYSTEMS AND METHODS FOR SORTING SAMPLES

CROSS-REFERENCES TO RELATED APPLICATIONS

This application claims the benefit of U.S. Provisional Application No. 60/424,898, filed Nov. 8, 2002, which is incorporated by reference in its entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates generally to efficient material handling, and more particularly to sample sorting for grouping compounds. By capably sorting compounds presented in multiple formats, back and forth within multiple footprint environments, according to predetermined sorting criteria, the compounds can be grouped into batches, facilitating high-throughput screening and other applications.

BACKGROUND OF THE INVENTION

Compound production is an important process in the drug discovery and drug development industry. To that end, combinatorial chemistry is one technique employed to produce thousands of different compounds in batch processes. Compound production approaches frequently utilize any of a number of different devices, systems, components and/or instruments for sample processing that typically necessitate the placement of samples in particular locations within varying, multiple footprint environments. Ordinarily, sample re-formatting must be performed in order to address this issue, a process that constitutes a significant bottleneck in the drug discovery and drug development industry. Thus, the efficient back and forth movement, and/or placement of samples, from one or more footprints to other, different footprints, would effectively streamline an otherwise time consuming and expensive process. This is particularly true when process unification for compound production is a primary objective.

In some cases, it is very important to efficiently sort and/or group compounds when both quantitative and/or qualitative data is the basis for desired downstream operations. Yet, although thousands of compounds can be produced, the compounds, which can differ in a number of ways, often must be equal in molar concentration to be useful in quantitative high-throughput screening experiments and other applications. Unfortunately, the process required to achieve equal molar concentrations for different compounds, and/or the process of sorting and/or grouping compounds qualitatively, represents yet another bottleneck in the drug discovery and development industry. This is due to the fact that existing methods and systems are laborious, inefficient and time consuming, particularly since they generally operate serially, rather than in parallel.

Currently, a number steps must be performed in order to achieve equal molar concentration for a batch of compounds, because the sample mass of individual compounds can vary considerably from one processed sample to another. Such steps can include determining a mass of each compound of interest, calculating a volume of solution to be added to each compound in order to produce a desired molar concentration, and adding the calculated volume to each compound of interest. Unfortunately, a number of these steps, are generally performed manually, a fact that is problematic for a number of reasons.

One problem is related to the fact that thousands of compounds may be under consideration at any given time. Therefore, scientists can be required to expend valuable time weighing compounds and sorting the compounds/material based on the mass of each compound. Furthermore, human error is always a possibility, and, therefore, a concern with manual methods. Thus, existing manual methods are generally labor intensive, slow and prone to error.

Another conventional approach utilized to achieve equal molar concentration for large numbers/batches of compounds involves placing the material/compounds of interest into wells of a standard configuration 96 well microtiter plate. Depending upon the mass and molecular weight of material/compound in each individual well, each individual well is suspended with a different amount of solvent to achieve samples of equal molar concentration. This process is also very time consuming.

Alternatively, the overall weight of individual microtiter plates is used to estimate the amount of a particular material/compound per well and a uniform volume of solvent can be added to every well. Unfortunately, this method is inaccurate, and therefore problematic, because the resulting differences in the amount (moles) of each material/compound used in a particular screen generally generates non-quantitative data.

Existing systems have utilized automation to reduce the time associated with sorting material, however, considerable problems persist. For example, Bohdan Automation manufactures machines that load and unload tubes from tube blocks into a weighing machine. However, this technology suffers from a number of shortcomings, including, for example, that the technology is very slow, inflexible, essentially limited to 4 plate and 12 plate set-ups, provides a read only system, and does not have the capability to sort back and forth between multiple formats, in multiple footprint environments, and/or re-array, based on mass.

Existing automated systems are oftentimes limited by the availability of particular plate formats, and therefore, they are generally inflexible in terms of their ability to handle various designs and types of material, samples/sample containers. Existing methods and systems are also slow and generally unable to flexibly and simultaneously move material/multiple containers to different locations. For example, when existing systems and devices move material/containers, they can be limited to simple two-dimensional, vertical and/or horizontal movement and therefore cannot be placed in a unifying compound production process. Further, they are unable to adaptively sort material, samples/sample containers with multiple footprint capability; that is, from one or more first footprint(s) to one or more second, different footprints, and optionally, from the second, different footprint(s), back to the original first footprint. Also, existing systems typically cannot flexibly rotate material, samples/sample containers as part of the movement within the transferring process. Additionally, existing systems are oftentimes unable to successfully move material from one location to another specified location while simultaneously tracking the final location of the material. Further, existing systems suffer from the limitations of providing read-only capability. Read-only systems are ineffective if a predetermined track or endpoint for material/containers is not known.

From the foregoing discussion, it is apparent that there is a substantial need for methods, systems and apparatus that will offer a tenable solution to the existing need to efficiently sort large numbers/batches of material/compounds. It is also apparent that such a method, system and apparatus should efficiently sort materials/compounds such that those having the same amount (number of moles), or other properties of interest, are grouped into a batch or unit. In doing so, batches or units of grouped material can be efficiently addressed with a relatively uniform amount of solvent. Further, sorted/grouped material can be efficiently processed with high-throughput technology. Such a method, system and apparatus would provide a tremendous time savings and produce reliable concentrations of a multitude of various material/compounds.

SUMMARY OF THE INVENTION

The present invention relates generally to efficient material handling, and more particularly to sample sorting for grouping compounds. By automatically sorting compounds according to a predetermined sorting criteria, the compounds can be grouped into batches that can be useful in high-throughput screening and other applications. In particular, the present invention relates to methods, systems and an apparatus for efficiently moving selected material, samples, and/or sample containers, to and/or from multiple holding units. The present invention can significantly increase the throughput of various processes and thereby enhance, e.g., compound production in the drug discovery and drug development industries.

In one aspect, the present invention relates to a method of sorting samples that includes a) providing at least one source unit, the source unit comprises a plurality of biological or chemical samples, which samples comprise at least one first footprint b) selectively transferring one or more of the plurality of samples to at least one destination unit, which destination unit comprises at least one second footprint, different from the first footprint, using at least one automatic sorting mechanism, based upon one or more selected criteria, and c) repeating (a)-(b) at least once.

In accordance with the present invention, a source unit is optionally designed in any of a number of different ways, and/or configured to have any of a number of different formats and/or footprints. Therefore, a source unit can be designed to include either a non-standard, and/or a standard format. In one embodiment, a source unit includes at least one tube holder configured in a non-standard format. A non-standard format includes a spatial arrangement, configuration, form, positioning, structure, and/or shape that conforms to a custom design. Optionally, a source unit includes at least one tube holder configured in a standard format. A standard format includes a spatial arrangement, configuration, form, positioning, structure, and/or shape that conforms to a size and shape that is commonly encountered. In particular, a standard format refers to a standard size, shape, and configuration of a microtiter plate. Specifically, the size, shape and/or footprint of standard 96 well, 384 well or 1536 well microtiter plates are contemplated; however, other standard sizes are also compatible with the present invention.

In one embodiment, at least one source unit includes at least one tube holder designed to include a plurality of apertures configured to correspond to a spatial arrangement of wells of a standard 96 well microtiter plate format, or a standard 384 well microtiter plate format. Optionally, a plurality of tubes (e.g., polypropylene tubes, etc.) is located in the plurality of apertures. Tubes made of other materials, and/or various types of containers, can be located in the plurality of apertures. Optionally, the plurality of samples comprises, or is contained within, a plurality of tubes.

In one aspect, the present invention provides a method that includes assigning at least one source code to at least one source unit. Optionally, the method includes assigning at least one source label to at least one source unit. A source code, and/or label optionally conveys information about the source unit, such as information indicating a specific location of at least one source unit with respect to an automatic sorting mechanism. Optionally, a source code and/or label, stores criteria information about each of the plurality of samples. In one embodiment, the method includes automatically reading the at least one source code. In another embodiment, one or more source codes, and/or source labels are read manually or optically. In another embodiment, information about the at least one source unit is stored in at least one database. In certain embodiments, the method further includes importing data relating to the tubes. In some of these embodiments, the imported data comprises, e.g., tare weights of the tubes.

In one embodiment, each of a plurality of samples include an associated sample code that stores detailed information about each of the plurality of samples. Optionally, each of a plurality of samples includes an associated sample label that conveys detailed information about each of a plurality of samples. Detailed information includes criteria information that is optionally accessed when selectively transferring one or more of the plurality of samples. Optionally, detailed information includes a final registry code of one or more of the plurality of samples, such that the final registry code stores sample processing information. In one embodiment, each of the associated sample codes is read as the transferring occurs. Optionally, each of the associated sample labels is read as the transferring occurs. In one embodiment, the detailed information about each of the plurality of samples is stored in at least one database.

In accordance with the present invention, a destination unit is optionally designed in any of a number of different ways, and/or configured to correspond to any of a number of different formats, format combinations, footprints and/or footprint combinations. Therefore, a destination unit can be designed to include either a non-standard and/or a standard format. In one embodiment, a destination unit includes a plurality of apertures configured in a non-standard format. A non-standard format includes a spatial arrangement, configuration, form, positioning, structure, and/or shape, that conforms to a custom design. Optionally, a source unit includes at least one tube holder configured in a standard format. A standard format includes a spatial arrangement, configuration, form, positioning, structure, and/or shape that conforms to a size and shape that is commonly encountered. In particular, a standard format refers to a standard size, shape, and configuration of a microtiter plate. Specifically, the size, shape, and/or footprint of standard 96 well, 384 well or 1536 well microtiter plates are contemplated; however, other standard sizes are also compatible with the present invention.

In one embodiment, a destination unit includes a plurality of apertures configured to correspond to a spatial arrangement of wells of a standard 96 well microtiter plate format or a standard 384 well microtiter plate format. Optionally, at least one destination unit is assigned at least one destination code. Optionally, at least one destination unit is labeled with destination unit information. A destination code, and/or label includes any marking in a system or communication network that involves the use of a message, specific words, letters, symbols, or various images that are assigned a particular meaning. Further, a destination code, and/or label includes any letters, and/or numbers or other symbols, either individually or in combination, that are used in a system to represent or identify something. For example, a destination code and/or label includes one or more magnetic ink lines of varying widths that can be read optically with a scanning device, and/or one or more groups of printed and variously patterned bars, spaces and/or numbers that are designed to be scanned and/or read into computer memory as identification for a coded/labeled object. In accordance with the present invention, a destination code, and/or label optionally include destination unit information, such as information that reflects a particular location of a destination unit, a sample, a sample container, a specific material or a tube. In one embodiment, the method includes automatically reading the at least one destination code. Optionally, the method includes automatically, and/or manually, reading a destination code, and/or label. In another embodiment, information about the at least one destination unit is stored in at least one database.

The present invention provides significant advantages over existing methods and systems by providing a method that flexibly operates with one or more source units formatted in either a standard or non-standard format, and/or, optionally, in combination with one or more destination units formatted in either a standard or non-standard format. In one embodiment, the source unit and the destination unit optionally have either the same, or different footprints.

In accordance with the present invention, optionally, at least one source unit includes at least one tube holder designed to have a plurality of apertures configured to correspond to a non-standard format, and at least one destination unit includes at least one tube holder designed to have a plurality of apertures configured in a non-standard format. Further, optionally, at least one source unit includes at least one tube holder configured in a non-standard format, and at least one destination unit includes at least one a tube holder designed to have a plurality of apertures configured to correspond to a spatial arrangement of a standard 96 well microtiter plate format, or a standard 384 well microtiter plate format.

In another embodiment, at least one source unit includes at least one tube holder designed to have a plurality of apertures configured to correspond to a spatial arrangement of a standard 96 well microtiter plate format, or a standard 384 well microtiter plate format, and at least one destination unit includes at least one tube holder designed to have a plurality of apertures configured in a non-standard format. In yet another embodiment, at least one source unit includes at least one tube holder designed to have a plurality of apertures configured to correspond to a spatial arrangement of a standard 96 well microtiter plate format or a standard 384 well microtiter plate format, and at least one destination unit includes at least one tube holder designed to have a plurality of apertures configured to correspond to a spatial arrangement of a standard 96 well microtiter plate format, or a standard 384 well microtiter plate format.

Another notable advantage of the present invention stems from its ability to selectively transfer samples, sample containers, material or various other entities, from one location to another, based upon selected criteria. In one embodiment, the selected criteria include one or more physical characteristics of at least one of the samples. Optionally, the physical characteristics include at least one mass of at least one of the samples, at least one volume of at least one of the samples, at least one structure of at least one of the samples, and/or at least one specific location of at least one of the samples in the at least one source unit. In one embodiment, the selected criteria are stored in at least one database. In some embodiments, the selected criteria comprise one or more sample descriptors (e.g., a level of sample purity or the like) and samples comprising at least one common sample descriptor are grouped together in one or more destination units. In these embodiments, samples comprising one or more different sample descriptors are optionally grouped in different destination units.

In one aspect, at least one database is integrally associated with, and connected to, at least one central processing unit. The database includes data/information corresponding to the plurality of samples or sample containers, the at least one source unit, the at least one destination unit, and/or the at least one automatic sorting mechanism. In one embodiment, the database is at least one central database that includes a body of information that is obtained from one or more sub-databases. A sub-data base includes a subset of data in a database that is used in a specific application. In one embodiment, the body of information is stored in a computer system. The information is stored in such a way as to be able to quickly and easily access and/or change the information as necessary. Optionally, the at least one central database can access and control various systems and components that are operably connected to the present invention. Further, optionally, the central processing unit is operably accessed via at least one operator interface.

The present invention overcomes the severe limitations and shortcomings of existing methods and systems that are generally limited to very specific plate formats, and/or are limited to movement in only one or two-dimensions. Advantageously, the present invention contemplates an automatic sorting mechanism that effectively interacts, and cooperatively operates with entities of varying size, shape, format, and/or footprint. For example, an automatic sorting mechanism in accordance with the present invention functions effectively in combination with one or more source units, and/or destination units that include either a standard, and/or a non-standard format. In one embodiment, at least one automatic sorting mechanism transfers one or more samples, or various other entities, to one or more specific locations while simultaneously moving in a three-dimensional manner along x-y-z axes.

In a preferred embodiment, the method includes selectively transferring one or more of a plurality of samples to at least one destination unit, using the automatic sorting mechanism. The transferring comprises placing the samples in one or more specified locations in the at least one destination unit. The method optionally includes selectively transferring one or more of a plurality of samples to any of a number of different specified locations. For example, optionally, the transferring comprises placing the samples in one or more specified locations in at least one holding areas. The method also optionally includes conveying information about the specified locations to at least one database. In one method, the repeating of (a)-(b) as described herein above includes transferring one or more of the plurality of samples to at least one additional destination unit in (b), or providing at least one additional source unit in (a), or both, wherein the additional source unit comprises an additional plurality of samples.

In one embodiment, at least about 48 source units are provided and the transferring includes transferring one or more samples from the at least about 48 source units to at least about 6 destination units. In one embodiment, an automatic sorting mechanism includes one or more associated carrousels, and the method includes mounting at least one source unit on at least one of the carrousels. Optionally, the automatic sorting mechanism includes one or more associated carrousels, and the method includes mounting a plurality of source units on at least one of the carrousels.

In accordance with a method of the present invention, the selective transferring conveniently produces large numbers of grouped/batched samples, sample containers, tubes, etc. that are useful in high-throughput screening environments. Optionally, a method includes grouping the samples into at least one batch according to similar or identical criteria. Also, optionally, a method includes arranging the samples into one or more discrete groups in the at least one destination unit. In one embodiment, a plurality of samples comprise, or are contained within, a plurality of tubes and the method includes grouping the samples into batches of up to about 96 tubes. Optionally, a method includes grouping the samples into batches of up to about 384 tubes.

Significantly, an automatic sorting mechanism in accordance with the present invention has enhanced dexterity that enables it to access, and/or engage/grasp material, samples/sample containers, such as tubes, and transfer them to one or more balances for weighing. Optionally, one method of the present invention includes i) weighing at least one sample, or at least one sample container, such as a tube, to obtain a first mass, the first mass comprises a tare, ii) adding a material to the sample or the tube, iii) weighing the sample or the tube to obtain a second mass, and iv) deducting the tare from the second mass to obtain a mass of the material. Therefore, the present invention provides efficient methods for automatically selecting, weighing, and transferring samples.

Beneficially, the present invention provides for the cooperative association, and operable coupling of a number of workstations, and/or processing areas. In one embodiment, one or more samples, or one or more sample containers are processed at one or more workstations, according to specified instructions, before the sample, and/or sample container is transferred. In another embodiment, one or more samples, or one or more sample containers, are processed at one or more workstations, according to specified instructions, after the sample is transferred. In yet another embodiment, a method includes suspending the sample using the automatic sorting mechanism, and processing the sample at one or more workstations as the sample is suspended.

The present invention provides an efficient read/write and tracking capability. This capability has significant advantages over existing methods and systems that generally provide read-only capability. In accordance with the present invention, optionally, various entities, such as material, samples, sample containers, source units, destination units, and other components can be efficiently labeled, and/or coded, and periodically receive updated labels, and/or codes. A label, and/or code can convey various types of information, and conveniently, can be read either manually or optically, and/or with an automated reading mechanism, at a number of different points in time. As a result, the various entities, and their specific location, can be quickly identified and tracked. Thus, the accuracy and reliability of the sorting method of the present invention is thereby enhanced. Further, in providing the ability to intermittently write on samples/sample containers such that they are properly labeled, and/or coded, the present invention provides more flexibility than existing methods and systems to take samples off-line for further processing with fewer associated risks. Advantageously, the present invention provides for positional encoding of samples/sample containers. Therefore, one or more specific locations of samples/sample containers can be tracked by sending location information to one or more text files/databases. The text files/databases can then be queried by an operator and the samples/sample containers can be sorted based on their location/position. The present invention can be used to physically sort a multitude of entities and the sorting can be based on any criteria available within one or more text files/databases.

In one embodiment of the present invention, a method includes labeling at least one source unit, and/or at least one destination unit, and/or at least one of the samples, or at least one container containing the sample, with source unit information, and/or destination unit information, and/or sample information, wherein the information is applied to the source unit, the destination unit, the sample, or to the container, with at least one labeling mechanism. One or more labels include any identifying information, including a code or image of any kind, a brand, a marking, a designation, a tag, a sticker, a stamp, an identification, a classification, and/or a name using letters, numbers, or a combination of both, and/or an encoded mark.

In another embodiment, updated information is applied after at least one sample, sample container, and/or material has been processed at one or more workstations. In another embodiment, updated information is applied after a sample, sample container, and/or material, is transferred. Further, optionally, one or more source units, and/or destination units are labeled/coded with updated information.

In accordance with the present invention, at least one labeling mechanism includes any labeling device, tool, machine, system of parts, instrument, appliance, or any component of the same, that applies, or facilitates the application of one or more labels and/or codes onto, or into a surface of an object. In one embodiment, at least one labeling mechanism includes at least one laser-etching unit or equivalent. A laser-etching unit includes any device, tool, machine, instrument, and/or appliance, or any component of same, that can produce a laser emission with an intensity sufficient to engrave various information, such as a written code, one or more magnetic ink lines of varying widths that can be read with a scanning device, and/or one or more groups of printed and variously patterned bars, spaces and/or numbers that are designed to be scanned and/or read into computer memory, an image of any kind, a brand, a marking, a designation, a tag, a sticker, a stamp, an identification, a classification, or a name using letters, numbers, or a combination of both, or an encoded mark, on metal, glass, or various other materials.

Optionally, at least one labeling mechanism includes at least one ink jet labeling unit or equivalent. At least one ink jet labeling unit generally includes any apparatus, mechanical or manual device, that applies ink onto a surface, including a printer that projects electrically charged droplets of ink onto an object, or any printing system in which electrostatically charged droplets of ink are guided by a computer to form images or characters. The term ink jet labeling unit also applies generically to any comparable printer or imaging device that forms characters or images onto objects or surfaces by deflecting drops of ink or other coatings, using any commonly accepted method.

Generally, any type of information can be applied to, or printed or etched on, the mulititude of entities, and their equivalents, that are optionally utilized in a method for sorting samples in accordance with the present invention. In one embodiment, the sample information optionally includes one or more of a sample code, a sample mass, a starting position of the sample, a destination position of the sample and/or a registration code of the sample, which registration code stores sample processing information. In another embodiment, the source unit information optionally includes any information that concerns a location of a source unit, or a location of any material, container, sample, or sample container that is located in, and/or associated with, the source unit. In yet another embodiment, destination unit information optionally includes one or more destination codes, and/or information that communicates a status, condition, contents, and/or a location of a destination unit.

In accordance with the present invention, labels, and/or codes are optionally read. Further, "read" information can be transmitted to one or more databases, and/or to one or more central processing systems. In one embodiment of the present invention, a method includes reading the sample information using at least one optical system reader. At least one optical system readers includes any device, machine, apparatus, tool, computer component, or unit, either separately or in combination, that can capture and interpret data in printed, handwritten, coded, or other visual forms. Optionally, an optical system reader captures and interprets various information, an image of some kind, a brand, a marking, a designation, a tag, a sticker, a stamp, an identification, a classification, or a name using letters and/or numbers. An optical system reader also optionally includes digital processing components that convert an optical signal into a digital signal, e.g., for storage in a digital database. In one embodiment, the method includes reading the sample information by manual/visual inspection. In accordance with the present invention, sample information, source unit information, and/or destination unit information, is optionally read using either at least one optical system reader, and/or by manual/visual inspection. Further, electromagnetic wavelengths such as RF (Radio Frequency), IR (Infrared) and/or UV (Ultraviolet) can be used to read labels and/or codes.

The present invention also provides a system for sorting samples that includes at least one source unit configured to receive a plurality of samples or sample containers, at least one sorting device, the at least one sorting device includes at least one automatic sorting mechanism, at least one holding fixture to receive the at least one source unit, at least one loading fixture to receive at least one destination unit, and, at least one central processing unit. The at least one central processing unit directs the repetitive transfer of one or more samples, or one or more sample containers, from the at least one source unit to the at least one destination unit, based upon one or more selected criteria. Optionally, the source unit and the destination units have different footprints.

In one embodiment, at least one source unit is assigned at least one source unit label, and/or code, in at least one central processing unit. Optionally, the source unit label, and/or code stores detailed information about the source unit, the plurality of samples, and/or the sample containers. Optionally, the system includes at least one automated mechanism for reading at least one source unit label, and/or code. Further, the source unit label, and/or code, is optionally read manually or optically. In one embodiment, at least one destination unit is assigned at least one destination label, and/or code, in at least one central processing unit. Optionally, the system includes at least one automated mechanism for reading the at least one destination code. Further, the destination label, and/or code are optionally read manually or optically.

In some embodiments, the central processing unit is configured to import data (e.g., tare weights of the sample containers, etc.) relating to the sample containers. Optionally, the selected criteria comprise one or more descriptors (e.g., a level of sample purity, etc.). In these embodiments, the central processing unit is typically configured to group samples, or sample containers, comprising at least one common descriptor together in one or more destination units. In some of these embodiments, the central processing unit is configured to group samples, or sample containers, comprising one or more different descriptors in different destination units.

In one embodiment, a plurality of samples, or sample containers are located in at least one source unit. Optionally, each of the plurality of samples, or sample containers have an associated sample code. Associated sample codes store detailed information about each of the plurality of samples or sample containers. In another embodiment, the system includes at least one automated mechanism for reading each of the associated sample codes. Optionally, sample codes are read manually or optically.

In certain embodiments, at least one source unit includes at least one tube holder configured in a non-standard format, and at least one destination unit includes at least one tube holder configured in a non-standard format. Optionally, at least one source unit includes at least one tube holder configured in a non-standard format, and at least one destination unit includes at least one tube holder with a plurality of apertures configured to correspond to a spatial arrangement of a standard 96 well microtiter plate format or a standard 384 well microtiter plate format.

In another embodiment, at least one source unit includes at least one tube holder with a plurality of apertures configured to correspond to a spatial arrangement of a standard 96 well microtiter plate format or a standard 384 well microtiter plate format, and at least one destination unit includes at least one tube holder configured in a non-standard format. Optionally, at least one source unit includes at least one tube holder with a plurality of apertures configured to correspond to a spatial arrangement of a standard 96 well microtiter plate format or a standard 384 well microtiter plate format, and the destination unit includes at least one tube holder with a plurality of apertures configured to correspond to the spatial arrangement of a standard 96 well microtiter plate format or a standard 384 well microtiter plate format.

In accordance with the present invention, one embodiment includes at least one source unit that includes at least one tube holder configured to receive at least one of the samples or at least one of the sample containers. Optionally, the tube holder includes a plurality of apertures configured to correspond to a spatial arrangement of wells of a standard 96 microtiter plate well format or a standard 384 microtiter plate well format.

In another aspect, the present invention provides at least one automatic sorting mechanism that includes one or more transferring units that move the samples, and/or the sample containers, to one or more specific locations while simultaneously moving in a three-dimensional manner along x-y-z axes. In one embodiment, the system includes one or more balances. The balances are configured to determine a mass of one or more samples, sample containers, or both. In accordance with the present invention, at least one automatic sorting mechanism cooperatively operates with the one or more balances. The automatic sorting mechanism transfers samples, sample containers, and various other specified entities, from one or more holding areas, to one or more balances. In one embodiment, the automatic sorting mechanism transfers one or more samples, or one or more sample containers from at least one source unit to a specific location in at least one destination unit. The automatic sorting mechanism optionally returns specified entities to an original, specific location, or transfers specified entities to a new, and/or different location.

In another aspect, the present invention provides a system for sorting samples that includes at least one labeling mechanism configured to automatically apply at least one label on at least one source unit, and/or at least one destination unit, and/or at least one sample or sample container. Optionally, the labeling mechanism is configured to automatically apply at least one code on at least one source unit, and/or at least one destination unit, and/or at least one sample or sample container. In one embodiment, the labeling mechanism includes at least one inkjet labeling unit or equivalent. In another embodiment, the labeling mechanism includes at least one laser etching unit or equivalent. The at least one laser etching unit etches one or more labels and/or one or more codes on at least one source unit, and/or at least one destination unit, and/or at least one sample or sample container. In one embodiment, the system includes at least one automated mechanism for reading the label. Optionally, the system includes at least one automated mechanism for reading the code. In one embodiment, information obtained from reading a label, and/or a code are transmitted to at least one database. Optionally, one or more labels, and/or codes are read manually or optically.

In accordance with the present invention, a system for sorting samples includes various associated workstations and/or components. For example, in one aspect, the system includes at least one fluid-handling unit. The fluid-handling unit dispenses or extracts a specified amount of fluid liquid to or from one or more samples, or one or more sample containers. In another aspect, the system includes at least one workstation. A workstation includes one or more areas that processes one or more samples, or one or more sample containers according to specified instructions, before the sample is transferred. Optionally, a workstation processes one or more samples, or one or more sample containers according to specified instructions, after the sample is transferred.

In one embodiment, the workstation includes at least one mass spectroscopy units. In another aspect, the system includes at least one holding station, which holding station receives one or more samples or sample containers, before the samples are transferred. In yet another aspect, at least one sorting device of the present invention includes one or more carrousels configured to receive at least one source unit or at least one destination unit. Optionally, a plurality of source units is located in the carrousels. Further, optionally, a plurality of destination units is located in the carrousels.

The present invention provides a system that includes at least one central database. The central database is integrally associated with at least one central processing unit and comprises data corresponding to a plurality of samples or sample containers, at least one source unit, at least one destination unit, and/or at least one sorting device.

BRIEF DESCRIPTION ON THE FIGURES

FIG. 1 is a flow diagram illustrating a method, system and apparatus for sorting samples in accordance with the present invention.

Figure 2:
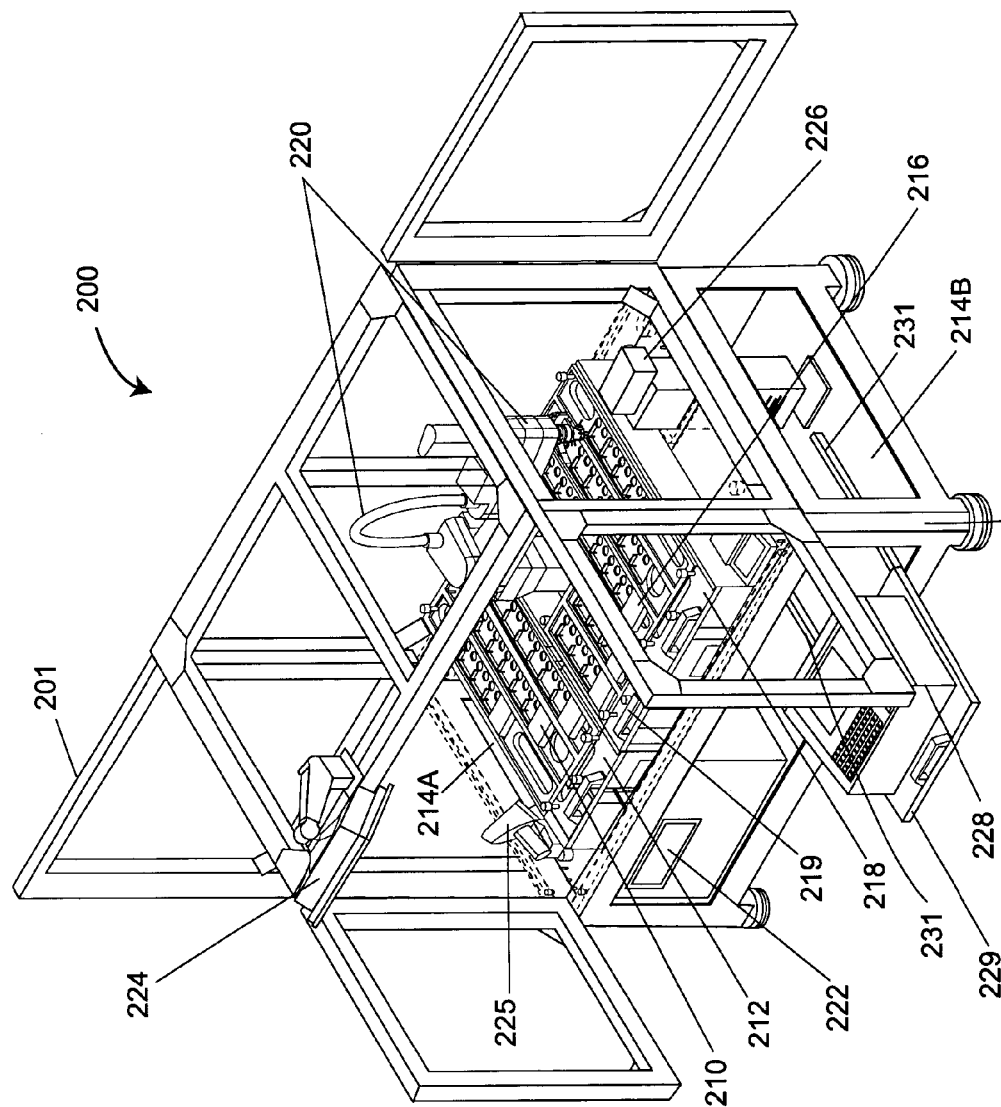

FIG. 2 schematically illustrates one embodiment of a sorting apparatus from a perspective view.

Figure 3:
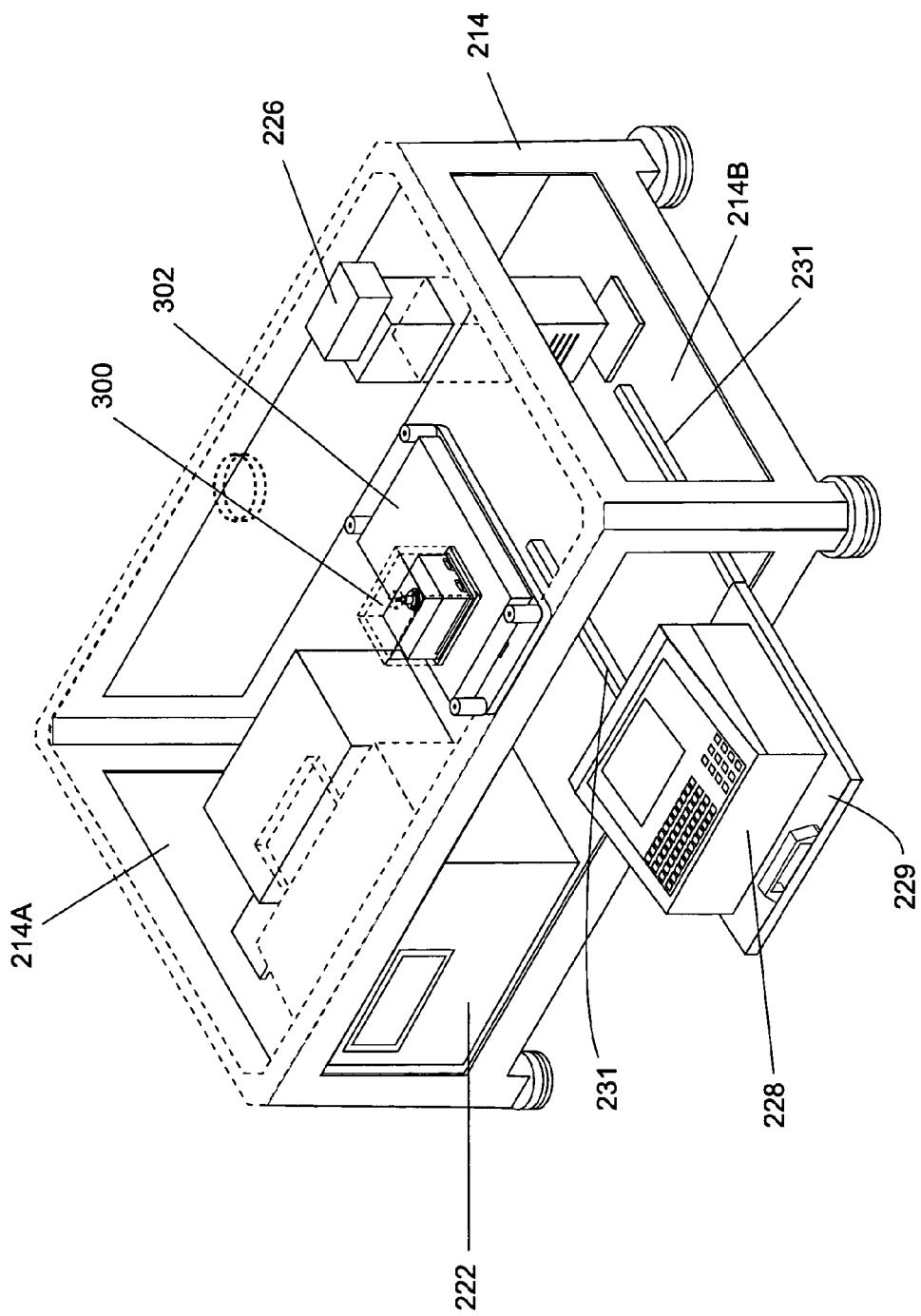

FIG. 3 schematically illustrates one embodiment of a lower section of a sorting apparatus from a perspective view.

Figure 4:
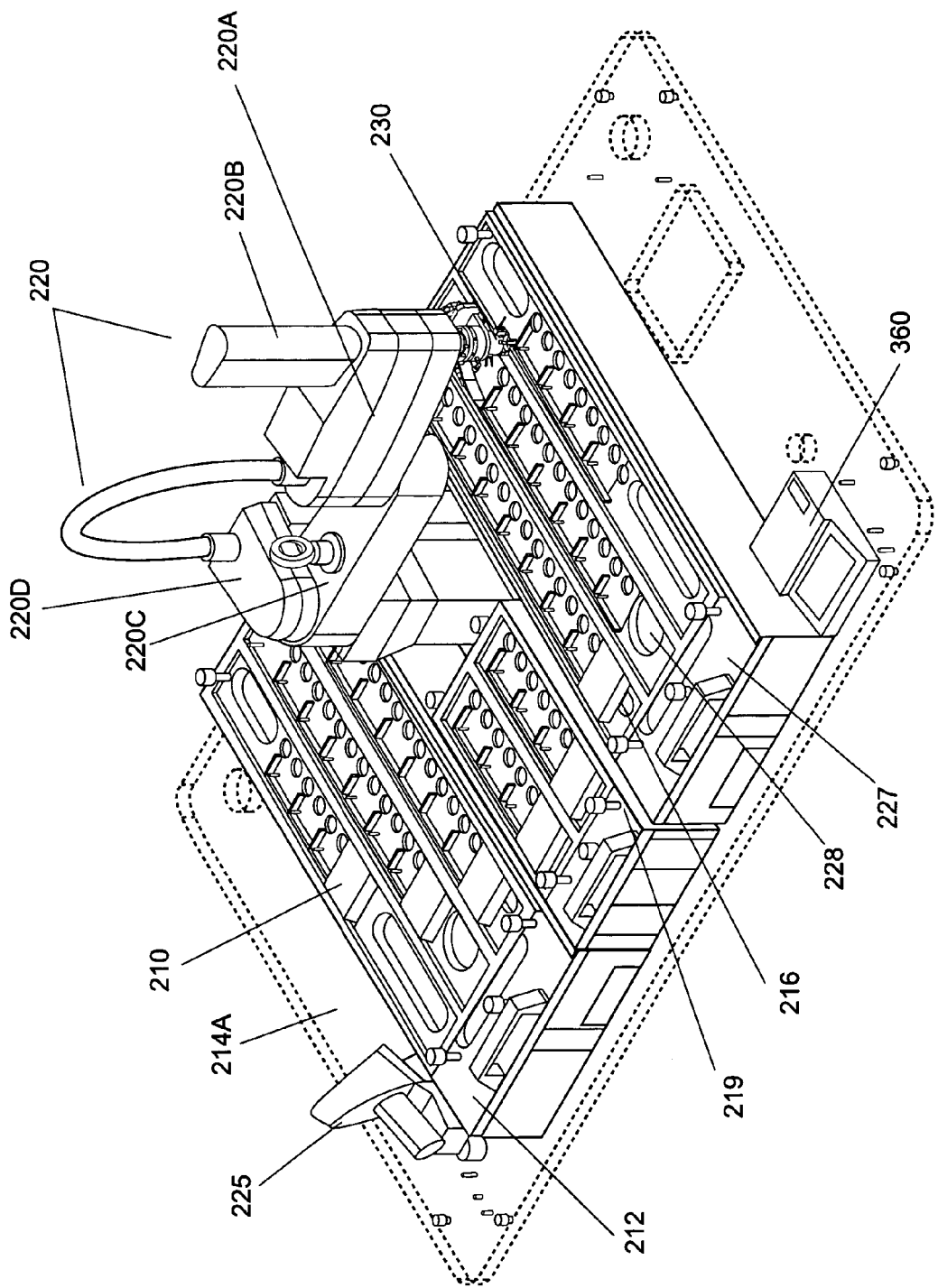

FIG. 4 schematically illustrates one embodiment of an upper section of a sorting apparatus from a perspective view.

Figure 5:
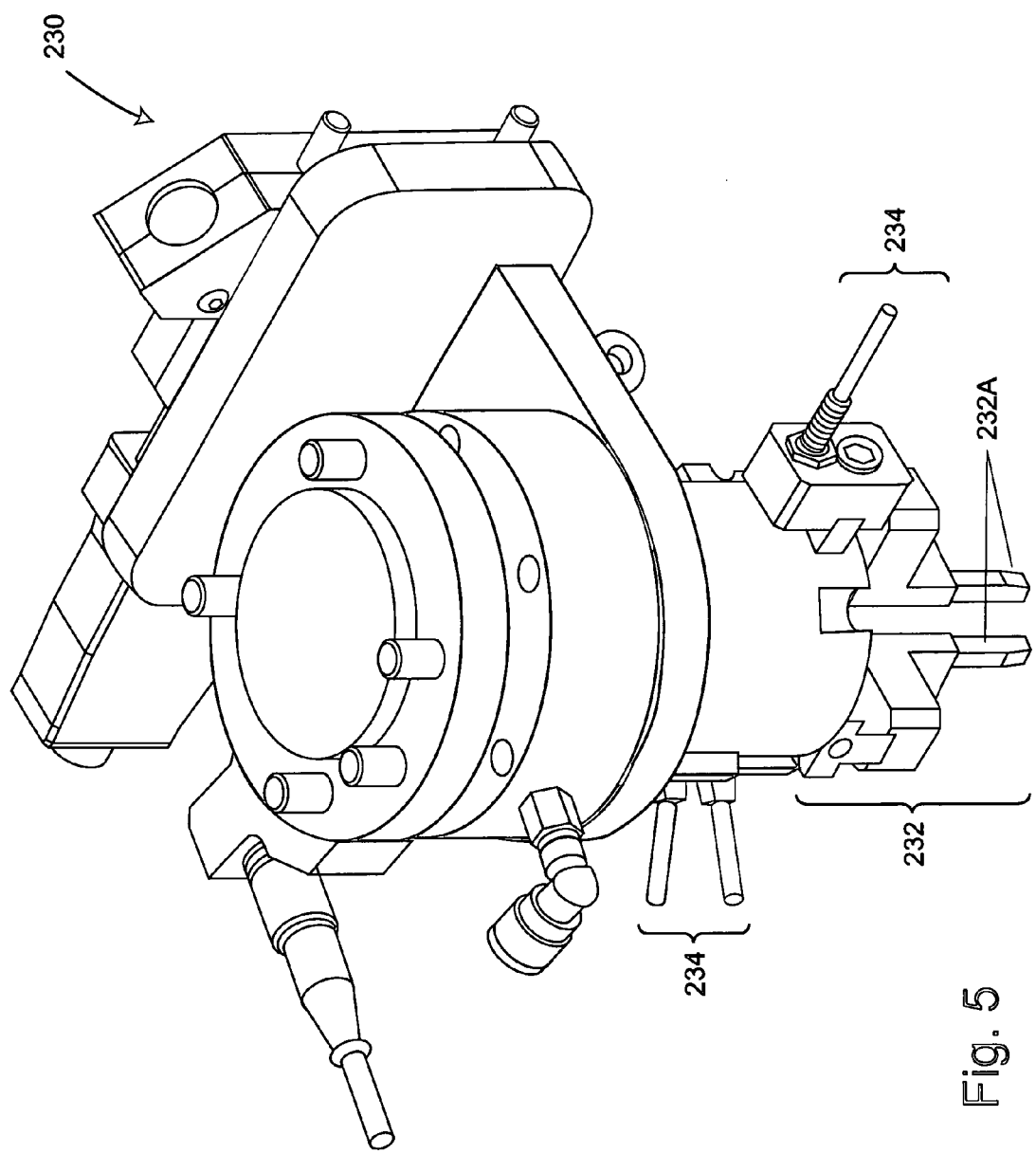

FIG. 5 schematically illustrates one embodiment of a engaging mechanism of an automatic sorting mechanism from a perspective view.

Figure 6:
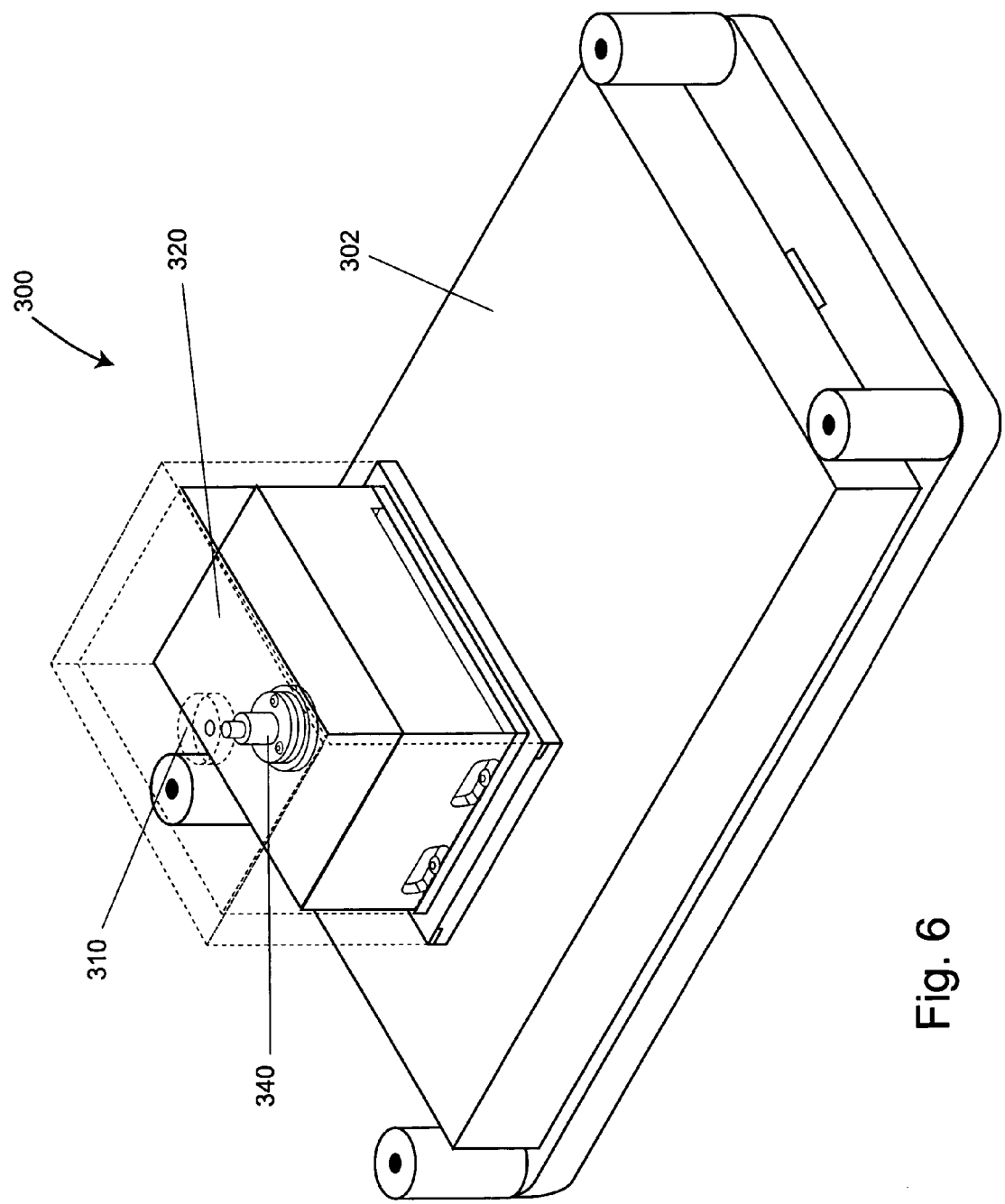

FIG. 6 schematically illustrates one embodiment of a stabilized balance from a perspective view.

DETAILED DESCRIPTION

Methods, systems, and apparatus for sorting samples in accordance with the present invention are provided. In one aspect, at least one source unit is provided. The source unit comprises a plurality of biological or chemical samples, the samples comprise at least one first footprint. The method includes selectively transferring one or more of the plurality of samples to at least one destination unit, the destination unit comprises at least one second footprint that can be different than the first footprint. The selective transferring occurs using at least one automatic sorting mechanism, based upon one or more selected criteria. Further, the method optionally and typically includes repeating the above, at least once.

Accordingly, a method, system and apparatus of the present invention overcomes the problems of conventional approaches by, e.g., describing an efficient, accurate, and flexible way of handling material. For example, the method, system and apparatus of the present invention address the existing need for an efficient and reliable way to obtain equi-molar concentrations of compounds that are then useful in quantitative high-throughput screening experiments and other applications. Further, the method, system and apparatus of the present invention provide enormous flexibility, including the ability to efficiently obtain the mass of any particular sample/sample container, to sort back and forth between multiple varying formats, to read and write information on samples/sample containers, to positionally encode samples/sample containers, and to track the location of the sample. The method, system and apparatus efficiently sorts samples/sample containers into groups according to any specified criteria. The sorted samples/sample containers, such as compounds, are then useful for desired downstream operations. Therefore, the existing problems related to the inefficiency, inaccuracy, and inflexibility associated with conventional methods are overcome by the present invention.

Definitions

Before describing the present invention in detail, it is to be understood that this invention is not limited to particular apparatus, systems, or methods, which can, of course, vary. It is also to be understood that the terminology used herein is for the purpose of describing particular embodiments only, and is not intended to be limiting. As used in this specification and the appended claims, the singular forms "a," "an," and "the" include plural referents unless the context indicates otherwise. Thus, for example, reference to "a sample" includes a combination of two or more samples, or the like. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set out below.

The term "aperture" refers to any opening, such as a hole, a space, an orifice, an indentation or cavity. The aperture can be any shape, e.g., circular, square, rectangular, triangular or the like. An aperture can encompass any opening appropriate for partially or fully containing a sample, a sample container, or other material so that it can be handled by a sorting mechanism described herein.

The term "automated reading mechanism" refers to any machine, device, system, or scanner that can optically receive a signal, a label, a code, or other information. The code or other information can be received remotely and optically, magnetically, electromechanically, electromagnetically (including RF (Radio Frequency), IR (Infrared) and/or UV (Ultraviolet)), or the like, depending on the detector used by the reading mechanism. An automated reading mechanism can also decipher or translate a signal or code and convey information to a database either directly, or via a central processing unit of a computer system. The automated reading mechanism as used herein can read any or all of a number of different codes associated with samples, sample containers, source units, sample destination units or the like and can convey the information to a subdatabase or a central database.

The term "automatic sorting mechanism" refers to any mechanical device, whether alone or connected to a computer system, or any part of a device or machine, such as a robotic arm or mechanical lever, that can grasp material, a sample or sample container, and move about multiple axes, in multiple dimensions, particularly in three-dimensions to transfer, locate, relocate, re-orient, invert, simultaneously change one or more positioning angles and/or orientations of one or more samples/sample containers, as the samples/sample containers are moved from one location to another, and effectively sort material, one or more samples, or sample containers from any starting group or batch to an ending batch based upon specific selection criteria. In the context of the present invention, one or more automatic sorting mechanisms can move about one or more axes, e.g., 1, 2, 3, 4, 5 or 6 different axes (e.g., rotational and/or translational axes), and sort from a first footprint to a second, different footprint, and then back to the first footprint, and/or re-array samples, etc. based on mass, or any of a number of different criteria.

The term "balance" refers to an instruments, device, or machine for determining weight or mass.

The term "batch" refers to a grouping of samples, sample containers such as tubes, or material in various containers where a quantity or number is taken together, or grouped together for a particular operation. Within the context of the present invention, samples, sample containers, and/or material can be introduced to the sorting system and/or device and processed, transferred, or sorted from one batch to another.

The term "carrousel" refers to a case, container, holding unit or mechanism that can contain one or more sample blocks, batches, or groups of material, samples, sample containers, tubes, or other items. As used herein, a carrousel can be loaded with a number of source or destination units to enhance a continuous flow to a sorting device.

The term "central database" refers to a body of information. The information can be stored in a computer system. A central database can also contain information from one or more sub-data bases (a subset of data in a database that is used in a specific application). The information is stored in such a way as to be able to quickly and easily access and/or change the information as necessary.

The term "central processing unit" (CPU) refers to a processor, central processor, mainframe, or any part of a computer that does most of the data processing. The CPU and memory from the central part of a computer to which the peripherals are attached. The CPU is the part of the computer that interprets and executes instructions and also controls other parts of the system. Generally, the CPU comprises a control unit, an ALU (arithmetic and logic unit) and memory (registers, cache, RAM and ROM) as well as various temporary buffers and other logic. The CPU fetches instructions from memory and decodes them to produce signals that control other parts of the computer. This may cause it to transfer data between memory and ALU or to activate peripherals to perform input or output. The term CPU can include various types of electronic equipment, particularly equipment that involves the controlled conduction of electrons, especially in a gas or vacuum or semiconductor, and can include various types of hardware, such as the mechanical, magnetic, electronic, and electrical components making up a computer system. In the context of the present invention, a computer can have several CPUs that may share other resources such as memory and peripherals. Additionally, one or more CPUs can control one or more robots, automatic sorting mechanisms and/or sorting devices, and/or use interface software to interact with one or more controllers that control the robots, automatic sorting mechanisms and/or sorting devices via a specified language.

The term "criteria information" refers to particular qualities of interest, and/or detailed information that can be accessed and used to selectively transfer one or more samples, sample containers, material and/or compounds. Criteria information can include information that pertains to one or more source units, destination units, holding units, and/or various other units.

The term "dampening quality" refers to the ability to reduce vibration, to mute, to muffle, to tone down or weaken, to reduce the amplitude of oscillation or waves. For example, in the context of the present invention, a dampening quality can soften a shock caused by any internal operation(s) of the automatic sorting mechanism /sorting apparatus, and/or by vibrations that are external to the operation of the automatic sorting mechanism/sorting apparatus, and/or by various other type of movement. Therefore, if a stabilized balance is mounted on a material that has a good dampening quality, the material will absorb or muffle various vibrations and thereby prevent the vibrations from negatively impacting the function and accuracy of the balance.

The term "destination code" refers to any marking in a system or communication network that involves the use of a message, specific words, letters, symbols, or various images that are assigned a particular meaning. A destination code can be any letters, and/or numbers or other symbols, either individually or in combination, that are used in a system to represent or identify something. The code can provide symbols that can be interpreted by a computer or user and can provide specific instructions to the computer or the user. The code is optionally a label that can be viewed manually, e.g., optically. The code can also be optically decoded/read by one or more remotely readable recording devices such those that employ various frequencies including RF (Radio Frequency), IR (Infrared) and/or UV (Ultraviolet). Further, various electromechanical methods and systems are compatible with the present invention. A destination code can include information that reflects a particular location of a destination unit, a sample, a sample container, a specific material and/or a tube.

The term "destination unit" refers to a container, a fixture, a device, a machine, a storage area, a final or intermediary position, a mechanical part or module, or any entity that receives a sample, a sample container, a material, or a tube so that they can be grouped together. In the present invention, examples of destination units include tube holders, or specimen racks. Further, a destination unit and a source unit in the context of the present invention can be the same in terms of structure and function.

The term "destination unit information" refers to one or more destination codes, or any information that communicates a status, condition, contents, and/or a location of a destination unit.

The term "detailed information" refers to any individual, particular, and/or specific image, structure, observation, distinguishing quality or property. In the context of the present invention, detailed information includes criteria information as described herein, or any information that can be accessed, and/or used when selectively transferring one or more samples in methods, systems and the apparatus of the present invention.

The term "engages" refers to the attaching, holding, clamping, gripping, grasping, securing, bringing or coming together, and/or interlocking of various items and/or components.

The term "final registry code" refers to any mark or label in a system or communication network that involves the use of a message, specific words, letters, or symbols that are assigned a particular meaning. The letters, and/or numbers, and/or symbols either individually or in combination, can be used in a system to represent or identify something. A final registry code can provide symbols that can be interpreted by a computer or a user and can provide specific instructions to the computer or user. A final registry code can also be a label that can be viewed manually, e.g., optically. In the context of the present invention, a final registry code can be considered detailed information, can be associated with each of one or more samples/sample containers, and can store sample processing information. A final registry code can also convey information that reflects the processing of a particular sample and indicate a result, and/or a determination, based upon that processing.

The term "fluid handling unit" refers to a device or system, which moves fluid from a source to a destination.

The term "footprint" refers to the general size of something, whether physical or virtual, to the amount of space that an object requires, or the floor or desk space taken up by a piece of hardware.

The term "holding fixture" refers to fixture that fully or partially contains a rack, a block, a group, or a batch of samples, sample containers, or material. In the context of the present invention, a holding fixture can be a separate unit or a component of an overall mechanical apparatus or system. In the context of the present invention, the holding fixture is designed to contain one or more source units.

The term "holding station" refers to any permanent or semi-permanent location, for a specified period of time, that facilitates the sorting process by providing an intermediary, short term, temporary location or resting position for material, samples, and/or sample containers within a sorting process. In the context of the present invention, for example, the holding station provides an intermediary, location for leaving a material, sample, and/or sample container between a source and a destination, while the sorting process occurs. Additionally, a holding station can serve as a storage area for material, samples/sample containers that do not meet specific quality standards.

The term "ink jet labeling unit" refers generally to any apparatus, mechanical or manual device that applies ink onto a surface, including a printer that projects electrically charged droplets of ink onto an object, or any printing system in which electrostatically charged droplets of ink are guided by a computer to form images or characters. The term ink jet labeling unit also applies generically to any comparable printer or imaging device that forms characters or images onto objects or surfaces by deflecting drops of ink or other coatings, using any commonly accepted method.

The term "label" refers to any identifying information, such as a code or image of any kind, a brand, a marking, a designation, a tag, a sticker, a stamp, an identification, a classification, or a name using letters, numbers, or a combination of both, or an encoded mark.

The term "labeling device" refers to any mechanism, machine, apparatus, instrument, tool, appliance, whether alone or as a component of a larger unit, that can apply one or more labels and/or codes, as described herein, to various objects and/or surfaces. A labeling device within the context of the present invention includes an ink-jet unit/printer, a laser etching unit (as commonly understood), an embossing or branding unit, and/or any other comparable units that can apply a permanent or semi-permanent label onto a surface. A labeling device can apply one or more labels/codes onto the surface of a sample, a sample container, or a tube.

The term "labeling mechanism" refers to any labeling device, tool, machine, system of parts, instrument, appliance, or any component of same, that applies, or facilitates the application of one or more labels/codes, onto or into a surface of an object.

The term "laser etching unit" refers to any device, tool, machine, instrument, and/or appliance, or any component of same, that can produce a laser emission with an intensity sufficient to engrave various information, such as a written code, an image of any kind, a brand, a marking, a designation, a tag, a sticker, a stamp, an identification, a classification, or a name using letters, numbers, or a combination of both, or an encoded mark, on metal, glass, or various other materials.

The term "loading fixture" refers to a fixture that contains a block, a group, or a batch of samples, sample containers, or material. In the context of the present invention, the loading fixture can be a separate unit or a component of an overall mechanical apparatus or system. A loading fixture is designed to contain destination units that may or may not contain samples, sample containers, or material.

The term "non-standard format" refers to a spatial arrangement, configuration, form, positioning, structure, and/or shape that conforms to a custom design. A non-standard format is typically organized for a particular purpose. In the context of the present invention, a non-standard format refers to the custom arrangement and ordering of any number of apertures of a source unit, a destination unit, a source block, a destination unit, and/or any holding unit, that are designed to contain one or more samples, sample containers, or material.

The term "optical system reader" refers to any device, machine, apparatus, tool, vision system, computer component, or unit, either separately or in combination, that can capture and interpret data in printed, handwritten, coded, or other visual forms, including data transmitted at various wavelengths such as, RF (Radio Frequency, IR (Infrared) and/or UV (Ultraviolet). An optical system reader can capture, optically decode and interpret various information, an image of any kind, a brand, a marking, a designation, a tag, a sticker, a stamp, an identification, a classification, or a name using letters and/or numbers, including one or more magnetic ink lines that can be read optically with one or more scanning devices, and/or one or more groups of printed and variously patterned bars, spaces and/or numbers that are designed to be scanned and/or read into computer memory as identification for one or more labeled objects. An optical system reader also optionally includes various electromechanical methods and systems and/or digital processing components that convert an optical signal into a digital signal, e.g., for storage in a digital database.

The term "positional encoding" refers to the ability to track various entities such as, samples, sample containers, material, compounds, and/or tubes by systematically sending information regarding one or more locations of the various entities to a text file/database.

The term "re-array" refers to a process, method and/or system that reorganizes, sorts, transfers, orders, groups, moves and/or relocates material, and/or samples/sample containers, and includes changing the actual physical location and arrangement of the material, and/or samples/sample containers. In the context of the present invention, the term includes the ability to reorganize, sort and/or transfer based on mass. Thus, for example, initially material, samples/sample containers can be arrayed such that they are arranged from heaviest to lightest mass within a microtiter plate holding unit. Subsequently, the material, samples/sample containers can be efficiently re-arrayed so that they are arranged from lightest to heaviest mass.

The term "sample" refers to any selected specimen, compound, drug, material, group of units, sample container, tube, test tube, product, chemical or biological substance, whether naturally-occurring or synthetic. In the context of the present invention, samples are optionally those substances that are encountered in the chemical pharmaceutical or biological industries.

The term "sample code" refers to any information, particularly sample information such as sample type, sample mass, sample volume, sample structure, sample location, sample processing results, that can be encoded and subsequently that can be deciphered via intervention with a scanner and/or an optical system reader, including a reader associated with a computer system, or that can be read and understood from visual observation. A sample code can be a set of instructions, e.g., computer instructions, a set of letters, numbers or symbols that represent assigned meanings, and can include one or more magnetic ink lines of varying widths that can be read/optically decoded with a scanning device. A sample code can also include one or more groups of printed and variously patterned bars, spaces and/or numbers that are designed to be scanned and/or read into computer memory as identification for a coded and/or labeled object. A sample code can be transmitted in various ways, including electromechanically and/or via electromagnetic wavelengths such as, RF (Radio Frequency), IR (Infrared) and/or UV (ultraviolet). In the context of the present invention, each of a plurality of samples can comprise an associated sample code. Also, each of the associated sample codes can store detailed information about each of the plurality of samples. The term sample code can include encoded or non-encoded sample information, detailed information, and/or criteria information.

The term "sample container" refers to any container designed or configured to contain a sample.

The term "sample information" refers to any data in the form of words, symbols, etc. that convey a status or condition of a sample, material, compounds, and/or sample containers. In the context of the present invention, sample information can include data regarding a material/compound type, a mass, a volume, various other physical characteristics, a specific location of a sample, a processing result of a sample or a final registry code designation. In the context of the present invention, "criteria information" and "detailed information" can be considered sample information.

The term "selected criteria" refers to information used to sort samples, sample containers, and/or material into groups that have similar qualities. Selected criteria can be various physical characteristics such as a mass or a chemical structure of the samples, sample containers and/or material. Selected criteria can also be specific locations of the different entities within certain source or destination units, or within certain processing areas.

The term "selectively transferring" refers to a particular process of transferring various units, such as samples, sample containers, and/or material within the sorting system and/or apparatus of the present invention. For example, selected criteria as described herein provides a basis for allowing one to access the criteria information to selectively transfer/sort samples according to similar qualities.

The term "sorting" refers to a process of grouping, arranging, ordering, and/or re-arraying.

The term "sorting device" refers to a machine, a mechanism, a tool, an electronic, pneumatic or manual component, an apparatus, an appliance, or any comparable instrument that can grasp, clamp, hold, or otherwise engage a unit and transfer the unit from one location to another. In the context of the present invention, a sorting device optionally includes a robotic arm, either as a separate entity or as an active component of a comprehensive machine. A sorting device also optionally includes a component that can be connected to a computer system and respond to the instructions of, e.g., a computer program.

The term "source code" includes any marking, label and/or information in a system or communication network that involves the use of a message, specific words, letters, or symbols, or various images that are assigned a particular meaning. A source code can be any letters, and/or numbers or other symbols, either individually or in combination, that are used in a system to represent or identify something and can be read, optically decoded and/or transmitted in various ways. For example, a source code and/or label includes one or more magnetic ink lines of varying widths that can be read with a scanning device, and/or one or more groups of printed and variously patterned bars, spaces and/or numbers that are designed to be scanned and/or read into computer memory as identification for a coded/labeled object. Methods and systems that employ electromagnetic wavelengths such as, RF (Radio Frequency), IR (Infrared) and/or UV (ultraviolet) can be used in the context of the present invention. Additionally, various electromechanical methods and systems are also compatible with the present invention. A source code can provide symbols that can be interpreted by a computer or user and can provide specific instructions to the computer or the user. A source code can be a label that can be viewed manually, e.g., optically. In the context of the present invention, a source code can store and/or convey various information, such as detailed information and/or criteria information about one or more source units, samples, sample containers, and/or material. For example, a source code can store and/or convey specific location information that identifies exactly where one or more samples/sample containers, etc. are located in one or more source units. In the context of the present invention, a source code can also indicate one or more particular locations of one or more source units, samples, sample containers, and/or material in proximity to an automatic sorting mechanism in a sorting apparatus.

The term "source unit" refers to any container, fixture, device, machine, storage area, final or intermediary position, mechanical part or module, or any entity that can receive and hold a sample, a sample container, a material, or a tube. A source unit can be configured in various ways to hold samples, sample containers such as tubes, or material. Examples of a source unit includes one or more tube holders, tube racks, and/or specimen holders that are either of a standard size and shape, or specially designed to comply with dimensions necessary to practice the present invention. In the context of the present invention, a source unit can comprise at least one tube holder that is designed to have a plurality of apertures configured to correspond to a spatial configuration of wells of, e.g., a standard 96 well microtiter plate format or a standard 384 well microtiter plate format. A source unit can also comprise one or more tube holders configured in a non-standard or custom design format. Further, a source unit and a destination unit can be structural and functional equivalents.

The term "source unit information" refers to any information that concerns the location of the source unit or the location of any material, container, sample, or sample container that is located in the source unit. Source unit information can also be detailed information about the physical characteristics of any material or sample that is located in the source unit.

The term "specified location" refers to a particular physical place, point, position, area or locale. In the context of the present invention, the specified location pertains to any location that can be a predetermined and desired location for a sample, sample container, or material. A specified location can be determined and/or designated manually. A specified location can also be determined and/or designated by accessing a database of a computer system.

The term "standard format" refers to a spatial arrangement, configuration, form, positioning, structure, and/or shape that conforms to a size and shape that is commonly encountered. In particular, a standard format refers to a standard size, shape, and configuration of a microtiter plate. Specifically, the size and shape of standard 96 well, 384 well or 1536 well microtiter plates are contemplated; however, other standard sizes are also compatible with the present invention. The standard format also refers to the spatial arrangement and ordering of a number of apertures of a source unit, a destination unit, a source block, and/or a destination unit that are designed to contain one or more samples, sample containers, or material(s).

The term "tare weight" or "tare mass" refers to a mass of a sample receptacle, in the absence of the sample. When a receptacle contains a sample or material and a gross mass is measured, a tare mass can be deducted from the gross mass to determine a mass of a sample or material.

The term "three dimensional manner" refers to movement that is not confined to a simple one-dimensional, or two-dimensional, vertical or horizontal motion. A three dimensional manner of movement provides the ability to move through multiple planes of space simultaneously.

The term "tube" refers to a container such as a cylindrical body made of glass, plastic, a polymer, metal or any appropriate material, designed to hold various substances. A tube may either be specifically designed for use with a source unit and/or destination unit of the present invention, or it can be any standard tube designed to hold any selected specimen, compound, drug, material, group of units, product, chemical or biological substance, either naturally-occurring or synthetic. In the context of the present invention, sample containers are particularly those that are commonly encountered in the pharmaceutical industry, for example, test tubes of varying sizes.

The term "tube holder" refers to a rack, or framework of any kind that can contain tubes. In particular, a tube holder is a rack that can hold samples, sample containers or material in a standard or a non-standard spatial arrangement.

The term "well" refers to a hole, aperture, hollow compartment or receptacle that is formed in a container, e.g. a well of a microtiter plate.

The present invention relates generally to methods, systems and apparatus for handling material. In accordance with the present invention, combinations of elements and components provide for efficient and accurate sorting of materials, based upon specified criteria. In particular, the present invention provides for high-speed sample sorting for grouping compounds. As a result of the present invention, samples can be automatically and efficiently sorted into groups based upon similar specified criteria. Further, large groups, or batches of samples with essentially the same molar concentration can be accurately generated and efficiently processed in parallel.

The present invention provides significant advantages over existing methods and systems in providing flexible, accurate, reliable and efficient sorting, and/or processing capability. In accordance with the present invention, one or more automatic sorting mechanisms cooperatively operate with various holding units that accommodate a multitude of different samples, sample containers, material, or various other entities. The automatic sorting mechanism capably accesses, and selectively transfers the samples, sample containers, and/or material based upon specific criteria. Advantageously, the present invention provides a multiple footprint sorting capability. For example, source units containing synthesized compounds and comprising a first footprint corresponding to standard 96 well microtiter plates can be presented to the automatic sorting mechanism of the present invention. The samples can then be sorted, according to any of a number of different criteria, into discrete groups comprising one or more second footprints, different than the first footprint, e.g., corresponding to standard 48 well microtiter plates. The sorted samples can then be processed in parallel, after which they can be sorted back to the original first footprint.

Significantly, the present invention optionally cooperatively operates in conjunction with one or more balances. Therefore, accurate mass determinations of samples/compounds can be efficiently obtained. Advantageously, the present invention provides read/write capability in providing for the systematic and comprehensive labeling, and/or coding of samples. The labels/codes can convey various information, and the information can be transmitted to one or more databases, and/or one or more central processing units and accessed via one or more operator interfaces.

As a result of the present invention, the overall accuracy and reliability of the sorting and/or processing of samples is enhanced. The present invention provides additional benefits by contemplating operative cooperation and coupling with a plurality of different associated workstations, processing areas, components, and/or functional units.

Flexible Design & Formats

Enormous flexibility and convenience subsists in the present invention which provides various holding units that are optionally designed, configured, and/or formatted to simultaneously hold samples, such as various compounds of interest, and/or sample containers, such as tubes, and cooperatively operate in conjunction with one or more automatic sorting mechanisms to generate sorted batches/groups of samples. In particular, the present invention provides holding units such as one or more source units, and/or one or more destination units, that are optionally configured to accommodate the samples or sample containers. Further, optionally, source units and/or destination units in accordance with the present invention can have either the same, or different footprints.

In one embodiment, at least one source unit, and/or at least one destination unit, are designed to hold various entities such as different types of material, a plurality of samples, sample containers, and/or compounds. For example, in one embodiment, at least one source unit, and/or at least one destination unit are tube holders that have a plurality of apertures and optionally, samples, material, sample containers, and/or compounds are placed in the plurality of apertures. In accordance with the present invention, at least one source unit and/or at least one destination unit optionally include a plurality of openings or apertures that are configured in either a standard, and/or, a non-standard format. For example, a configuration of a source unit, and/or destination unit, such as a tube holder, conforms to a standard format when apertures of the tube holder correspond to, or axially align with a spatial configuration of a standard 96 well microtiter plate format, e.g., 8×12 rows/columns, or a standard 384 well microtiter plate format. Advantageously, the present invention provides the ability to quickly and efficiently change from one format to another. For example, hardware and software components of the present invention enable a smooth transition from a sorting method that employs a 96 well format to one that employs a 192 well and/or a 384 well format.

Additional advantages of the present invention are associated with the ability to efficiently and accurately organize, manage, select, sort, and/or process samples, and/or sample containers. This is extremely advantageous, particularly in the drug discovery and drug development industries because large numbers of compounds/samples are typically generated, and because these samples generally differ from one another with respect to any number of different factors or criteria. Therefore, these generated compounds/samples are typically organized, sorted, grouped into batches if they are to be efficiently processed, and/or evaluated using high-throughput technology. Significantly, in one embodiment, at least one sample, and/or sample container is selectively transferred from at least one source unit to at least one destination unit using at least one automatic sorting mechanism, based upon specified criteria. Furthermore, the automatic sorting mechanism of the present invention includes the ability to simultaneously access, engage, transfer and/or sort a multitude of samples. In the context of the present invention, samples can be selectively transferred based upon a material type, a mass, a volume, various other physical characteristics, and/or a specific position of the sample in the source unit.

Systems Logic

Further advantages of the present invention exist due to the fact that the methods, systems, and apparatus of the invention include optional coupling with one or more databases that can receive various data or criteria information. In one embodiment, one or more central processing units (CPU(s)) can access the information contained in the one or more databases, as well as provide the ability to monitor and control various functions within the methods, systems, and apparatus. Further, one or more user interfaces provide for significant interactive capability.

As noted herein, essentially any component of the system can be coupled to an appropriately programmed processor or computer that functions to instruct the operation of these components in accordance with preprogrammed or user input instructions, receive data and information from these components, and/or interpret, manipulate and report this information to the user. As such, the computer or processor is typically appropriately coupled to one or more components (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the system carry out the desired operation. The computer or controller then receives data from the one or more sensors/detectors included within the system, and interprets the data, either providing it in a user understood format, or using the data to initiate, e.g., controller instructions, in accordance with the programming, e.g., such as in monitoring and control of flow rates, temperatures, applied motor current or voltages, and/or the like.

In the present invention, the computer or controller typically includes software for the monitoring of materials in the system. This can include spreadsheet programs, database programs, inventory programs or the like. Additionally, the software is optionally used to control injection or withdrawal of material to/from the sample receiving elements, mixing or sonication of samples, fraction collector functions or the like.

Robotics

In accordance with the present invention, the automatic sorting mechanism can be essentially any mechanical device, such as a robotic arm or a mechanical lever that can accurately engages/grasps and transfers material, samples/sample containers, as well as performs various other tasks. Any of a variety of traditional robotics can be employed to transfer samples, and/or sample containers, to and/or from source units, and/or destination units, between any holding unit, carrousel, and work stations. Such robotics can include robotic armatures, grasping components, conveyor systems (e.g., conveyor belts, etc.) or the like. Typically, robotic components are coupled to a control system that directs sample/sample container movement between source and destination units, workstations, and/or sample/sample container tracking within the system.

Many such robotic components are commercially available. For example, a variety of automated systems are available from the Zymark Corporation (Zymark Center, Hopkinton, Mass., USA), which utilize various ZYMATE® systems, which can include, e.g., robotics and fluid handling modules. Similarly, suitable robotics are also available from, e.g., CRS Robotics Corporation (Burlington, Canada). Moreover, the ORCA® robot, which is commonly used in a variety of laboratory systems, e.g., for microtiter tray manipulation, is also commercially available, e.g., from Beckman Coulter, Inc. (Fullerton, Calif.). Another set of robots is available from Stäubli Corporation (SC, U.S.A.), which provide good freedom of movement for the arms of the robot. In addition, the auto and electronics industry provides sophisticated robotics that can be adapted to the systems herein. General introductions and resources related to robotics can be found on the internet at (www.) robotics.cs.umass.edu/robotics.html; ri.cmu.edu/; robotics.stanford.edu/ and many other sites.

Advantageously, in the present invention the automatic sorting mechanism can move effectively in three dimensions to transfer, locate, relocate, and sort material. Further, the automatic sorting mechanism can optionally access, and/or engage, every aperture, sample/sample container in each source unit or each destination unit that is presented. In accordance with the present invention, samples can be provided any number of times and the selective transfer of samples can be repeated as many times as necessary to obtain a desired result.

In one embodiment, one or more balances can be operably coupled to the automatic sorting mechanism. As a result, the automatic sorting mechanism selectively transfers designated samples/sample containers, and/or material to the one or more balances so that a mass determination can be obtained for any selected sample/compound. Optionally, in one embodiment, one or more samples/sample containers are weighed, a first mass is obtained, the first mass comprising a tare, the samples/sample containers are weighed again to obtain a second mass after a material has been added, and the tare is deducted from the second mass to obtain a mass of the material.

An additional advantage of the present invention is that various components of the methods, systems and apparatus, such as samples, sample containers, source units and destination units, can optionally be labeled, and/or coded, with various information/data either before, during, or after sorting occurs.

In one embodiment, the data that can be labeled/coded on samples, sample containers, source units and/or destination units can include information regarding, e.g., material/compound type, mass, volume, various other physical characteristics, specific location(s)/position(s) of a sample/sample container within a source and/or destination unit, specific location(s) of a source and/or destination unit and/or information reflecting the nature of any processing that one or more samples receive.

Another advantage of the present invention is that the label/code information can be updated. In other words, when any of the label/code information changes, the new information can be added to the various entities such as one or more samples, sample containers, source units and/or destination units.

Conveniently, the various entities can be manually/visually read, and/or scanned/read using one or more optical system readers at any point in the sorting process. Further, when the entities are scanned with an optical system reader, information can be sent to a database. Consequently, source units, destination units, samples, and/or sample containers can be conveniently and efficiently tracked throughout the entire sorting process.

Another advantage of the present invention is that the automatic sorting mechanism can be operationally coupled to a multitude of carrousels, workstations, and/or processing areas. Consequently, the automatic sorting mechanism can transfer various entities such as samples, sample containers and/or compounds from a source and/or destination unit to a processing unit, optionally suspend samples/compounds as processing occurs, subsequently return the entities to their original location, or relocate them to a different location or position.

In addition to sample processing components, any of a variety of sample production, treatment, processing and purification systems can be incorporated into the automated systems of the invention. These can include, e.g., cell fermentation apparatus which produce cells to be delivered to a sample receiving region, sample/fraction collectors which process materials from the sample receiving region, refrigerated modules that store samples and sample materials, analysis stations that perform sample or sample component analysis (e.g., mass spectroscopy equipment, gel electrophoresis apparatus, capillary electrophoresis equipment, photodiodes or photo-emitter arrays, microscope stations, cell sorters, flow cytometers, FACS equipment, DNA chips, nucleic acid or protein blotting stations, 2-D electrophoresis stations, etc.), and the like. Many such components are set forth in the references provided herein or otherwise known in the art, and are commercially available.

By sorting samples in accordance with the present invention, the resulting grouped samples, such as tubes containing compounds, can be filled in parallel with one or more high-speed fluid handling devices to achieve samples of equal molar concentration. The grouped samples can then be utilized in quantitative high-throughput processing systems. Additionally, the present invention efficiently sorts large numbers of individual compounds into discrete groups or batches based on various qualitative data, e.g., predetermined sorting criteria such as mass, volume, structure, and/or other physical characteristics so that they are useful in various desired downstream operations, such as various assays, purification processes, or other scientific applications.

Example Embodiments

The present invention provides methods, systems and an apparatus that can be used in conjunction with a number of associated components and processing systems. In the following paragraphs, the present invention is described in detail by way of example with reference to a number of figures. Throughout this description, the embodiments and examples shown are not to be considered as limiting the scope of the present invention. Many equivalent embodiments will be apparent to one skilled in the art.

Described below are: I. A method and system for sorting samples, and II. The functions of an automated sorting apparatus.

I. A Method and System for Sorting Samples

To further illustrate the present invention, refer now to the following description in conjunction with the accompanying figures. FIG. 1 is a flow diagram illustrating a method and system of sorting samples in accordance with the present invention. As shown in FIG. 1, a source unit can contain samples and/or sample containers and be provided to one or more automatic sorting mechanisms via step 103. In one preferred embodiment, a plurality of samples/compounds are placed in individual tubes, placed in one or more source units and delivered to the automatic sorting mechanism. A source unit is placed in a specific position in proximity to the automatic sorting mechanism, and the physical coordinates of the specific position are transmitted to a database/text file. In one embodiment, a source unit includes a tube block designed to hold 96 tubes in an 8×12 format, comprising a footprint that corresponds to a standard 96 well microtiter plate, and with an associated text file containing various information about the source unit, and/or about each of the samples contained in the source unit. Optionally, each sample is labeled and/or coded with various information.

A determination can be made whether a label and/or code is to be applied to, and/or etched on samples and/or sample containers via step 105. Samples/sample containers are labeled/coded with sample information via step 107 and the sample information can be directed to a database/text file via step 109. A determination is also made whether a source unit is to be labeled and/or coded via step 111 and a source unit can be labeled and/or coded with information via step 113. The information can be directed to a database via step 115.

Optionally, the samples/sample containers are labeled, and/or coded before being placed in the source unit. Also, optionally the source unit is labeled, and/or coded, before being provided to the automatic sorting mechanism. For example, a sample container such as a tube can be labeled and/or coded with data/information that indicates the type of material contained in the tube, the mass of the material contained in the tube, a determined volume of the material, or various other physical characteristics. The tube can be labeled and/or coded with other pertinent information as well. In one embodiment, each sample/sample container, e.g., each tube in a source unit, is labeled and/or coded with specific location information that identifies exactly where each sample/tube is located in the source unit. Further, the specific location information of each sample/tube is conveyed to one or more text files/databases such that each sample/tube is positionally encoded. Therefore, specific location information regarding each sample/tube is systematically tracked. Further, one or more text files/databases are optionally queried and each sample/tube is sorted based on its position/specific location. Also, if any processing has occurred, a final registry code/label can be applied onto, or etched onto the tube to reflect the nature of that processing. A source unit can also be labeled and/or coded with various information, such as information regarding its relative placement, or specific position in proximity to the automatic sorting mechanism, and information about any material, samples or sample containers contained in the source unit.

A determination is made whether one or more source units, samples/sample containers are to be read and/or scanned via step 117. A labeled/coded source unit, sample/sample container can be read and/or scanned via step 119. The reading or scanning can be performed manually or optically, and/or with an automatic reading mechanism, such as a scanner. Information obtained from the reading and/or scanning process can be directed to a database/text file via step 121.

Samples/sample containers are selected according to specified criteria via step 123 and a determination can be made whether to weigh selected samples via step 125. Selected samples/sample containers are accessed by an automatic sorting mechanism and optionally weighed on one or more balances via step 127. In one embodiment, at least one sample, such as a tube, can be weighed on a balance to obtain a first mass. The first mass constitutes a tare. A material/compound can then be added to the tube, after which a second mass can be obtained. Further, the tare can be deducted from the second mass to obtain a mass of the material/compound. In accordance with the present invention, information regarding a mass determination of samples/sample containers can be directed to a database via step 129.

In certain embodiments, software that implements aspects of the methods described herein, such as import file/database generation, includes the capability of importing, e.g., tare weights of empty tubes along with the other data contained in the import file. This allows the user to record tare weights for batches of tubes, store the data, and then, e.g., at a later date, generate an import file with tare data associated with compounds data for each tube. In these embodiments, the remainder of the processes (e.g., net weight, sorting, etc.) can then be carried out for the working set.

Next, via step 131, samples/sample containers can be selectively transferred to a destination unit using the automatic sorting mechanism and sample information can be directed to a database via step 133. In a preferred embodiment, a user provides one or more empty destination units to a specific location with respect to the automatic sorting mechanism and the physical coordinates of the specific location are transmitted to a database/text file. Significantly, destination units optionally comprise any of a number of different formats, and optionally comprise one or more footprints that are different than the footprint of the source unit. A determination is made whether a destination unit, and/or selectively transferred samples/sample containers are to be labeled/coded via step 135. A destination unit, samples/sample containers are labeled, and/or coded via step 137 and information is optionally directed to a database via step 139.

To further illustrate, in some embodiments of the invention, tube sorting to destination units (e.g., output plates, etc.) is based upon one of the precursor data fields, which allows for grouping of tubes with a common descriptor (e.g., purity class or the like) into new plates. To ensure that these groups do not share space in the same plate, the software optionally directs the sorting such that tubes are moved to new consecutive plates until all tubes for that group (e.g., a particular purity class, etc.) have been moved. The next group will typically start in the first well of the next consecutive plate, even if the previous plate is not completely filled according to these embodiments.

In one preferred embodiment, one or more labels and/or codes are recorded as destination units are loaded into one or more loading fixtures. One or more text files are queried as an operator identifies and selects specific source units and specific samples. A specific location of each of a plurality of samples is identified and designated for transfer. The automatic sorting mechanism sequentially transfers selected tubes from one or more source units to one or more destination units. In a preferred embodiment, sample containers, such as tubes are selected for transfer and one or more databases are simultaneously updated with information regarding one or more different locations for each transferred tube. Selective transfer, or sorting, continues until all of the selected tubes are transferred from source units to destination units.

A decision can be made to process selected samples via step 141. Samples can be processed at various associated workstations via step 143, and information regarding the nature of the processing, the samples/sample containers involved, the location of the samples/sample containers and various other types of information can be directed to a database/text file via step 145. Optionally, samples are transferred to one more holding areas/stations either before, and/or after sorting has occurred when they fail to meet quality standards. Sorted and/or grouped samples/sample containers are removed via step 147 and steps can be repeated as desired. Additionally, a central database can access, manage and control any of the databases described herein and any aspect of the method, system and apparatus of the present invention via step 149.

An operator optionally removes fully loaded destination units and replaces them with empty destination units as needed. The process is repeated until all samples/tubes are transferred into desired groups or batches. For example, a large group of synthesized, unpurified compounds, with varying characteristics, can be introduced to the automatic sorting mechanism in one or more source units. Each source unit comprises at least one first footprint, e.g., one or more that correspond to standard 96 well microtiter plates. The compounds are weighed and subsequently sorted according to mass, using the automatic sorting mechanism, into one or more destination units comprising at least one second footprint. Notably, the second footprint(s) can be different than the first footprint(s), e.g., one or more that corresponds to a standard 48 well microtiter plate, e.g., 8×6 rows/columns; that is, ½ of a standard 96 well microtiter plate. The sorting conveniently groups all compounds requiring similar volumes of solutions together, thereby facilitating parallel filling using conventional fluid handling devices. The compounds are then processed, e.g., purified, in parallel. Compounds that fail to meet quality standards can be placed in one or more holding areas/stations, using the automatic sorting mechanism. Significantly, purified compounds can be sorted back to the original, first footprint; that is, to one corresponding to standard 96 well microtiter plates, using the automatic sorting mechanism.

II. Automated Sorting Apparatus

Referring now to FIG. 2, a perspective view of one embodiment of sorting apparatus 200 is illustrated. Although FIG. 2 schematically depicts a mechanical arrangement with components in particular locations, the present invention optionally includes various other arrangements. As depicted in FIG. 2, sorting apparatus 200 can optionally be encased within interlocking enclosure 201 that forms an exterior shroud and framework for sorting apparatus 200. In one embodiment, interlocking enclosure 201 is operationally and mechanically coupled to sorting apparatus 200 such that interlocking enclosure 201 functions as a safety cage and provides operational safety. In such an embodiment, interlocking enclosure 201 prevents sorting apparatus 200 from operating any automatic components if interlocking enclosure 200 is in an open position, e.g., as shown in FIG. 2. In another embodiment, interlocking enclosure 201 functions as an air flow insulator by protecting the interior of sorting apparatus 200 from unwanted air movement that could interfere with the accuracy of any measurements performed within sorting apparatus 200. Optionally, and particularly important when light sensitive material/samples are involved, interlocking enclosure 201 is tinted, shaded, colored, and/or coated with one or more colors and/or hues to obscure transmission of light. In one embodiment, an opening can be made in interlocking enclosure 201 so that a hepa-filter (not shown) can be coupled to interlocking enclosure 201 to provide a filtered air environment inside interlocking enclosure 201.

FIG. 2 illustrates source unit 210 located in holding fixture 212. As shown, holding fixture 212 is designed to hold multiple source units. Holding fixture 212 can be flexibly mounted and removably attached in a conventional manner on an upper platform portion 214A of horizontal platform 214. Therefore, holding fixture 212 can be securely coupled to upper platform portion 214A while retaining the ability to be removed as a single unit holding multiple source units, if desired. As FIG. 2 illustrates, destination unit 216 can be located in loading fixture 218. As shown, loading fixture 218 is designed to hold multiple destination units. Loading fixture 218 can be flexibly mounted and removably attached in a conventional manner on upper platform portion 214A of horizontal platform 214. Loading fixture 218 can securely coupled to platform 214. Loading fixture 218 can also be removed as a single unit holding multiple destination units if desired. FIG. 2 schematically illustrates holding station 219 that can be flexibly mounted and removably attached on horizontal platform 214. Holding station 219 can essentially be a designated location or area, either permanent or semi-permanent that can receive one or more samples or sample containers. Holding station 219 can also be located outside of the general area that constitutes horizontal platform 214. As shown, holding station 219 is designed to optionally hold one or more source units 210 and/or one or more destination units 216.

FIG. 2 schematically illustrates automatic sorting mechanism 220 vertically situated and strategically interposed between holding fixture 212 and loading fixture 218. One advantage of sorting apparatus 200 stems from the fact that automatic sorting mechanism 220 can move in a three dimensional manner, in other words, it can perform x-y-z movement. In one embodiment, automatic sorting mechanism 220 can flexibly move about six different axes. Optionally, automatic sorting mechanism 220 can reorient samples, samples containers, and/or various holding units at various positions. For example, automatic sorting mechanism 220 can rotate one or more samples/sample containers to four different places at 90° angles. In one embodiment, automatic sorting mechanism 220 can be controlled by a central processing unit (CPU) 222. CPU 222 can be used to access, monitor and control a number of functions in the sorting apparatus 200. For example, CPU 222 can access, monitor and control sorting, accessing and transferring data from one or more databases, directing samples or sample containers to one or more workstations and directing one or more samples or sample containers to one or more fluid handling devices. An operator can interact with CPU 222 via operator interface 224 that comprises, e.g., a touch screen panel.

As depicted in FIG. 2, optionally, labeling device 226 can be cooperatively connected to sorting apparatus 200. In a preferred embodiment, labeling device 226 is a laser etching unit that is operationally coupled to sorting apparatus 200. Labeling device 226 is optionally an inkjet unit, and/or any comparable device, unit, or technique that can apply, or etch, one or more labels, and/or one or more codes on one or more surfaces of one or more samples, sample containers, source units, and/or destination units within sorting apparatus 200. As shown, sorting apparatus 200 is designed to optionally hold multiple labeling devices. Therefore, either one or more laser etching units, and/or one or more inkjet units, and/or one or more comparable mechanisms/devices can be cooperatively connected and operated with sorting apparatus 200.

Automatic sorting mechanism 220 is designed to access one or more labeling devices. For example, automatic sorting mechanism 220 can engage/grasp a selected sample and/or sample container, such as a tube located in either a source unit, a holding unit, a destination unit, a processing area, a carrousel, or other associated location, and transfer the tube to a particular location in front of labeling device 226 such that the labeling device can apply, and/or etch, a label and/or a code on the tube. Automatic sorting mechanism 220 can also return the tube to its original location, or transfer the tube to a different location.

In one embodiment, optionally, one or more labels reflecting sample information and/or one or more sample codes can be applied to, and/or etched on, one or more samples and/or sample containers, such as tubes. Sample information can be detailed information about each of a plurality of samples that can be placed in or interfaced with a sorting apparatus. Detailed information can include data regarding one or more physical characteristics, such as a mass determination, a molecular structure, a material/compound type, and/or a volume. Detailed information can also be data regarding one or more specific positions or locations of one or more samples, sample containers, material/compounds in a sorting apparatus, in a source unit, in a holding unit, in a destination unit, in a processing area or workstation, in a carrousel, or information about previous storage locations or previous processing. A sample code can embody, in coded and/or non-coded format, any sample unit information and/or other information as well. A sample information label and/or a sample code can be read manually and visually, and/or automatically read using an automated mechanism, such as a scanning device.

In one embodiment, one or more labels reflecting source unit information and/or criteria information and/or one or more source codes can be applied to and/or etched on one or more source units. Source unit information can be information about a location of the source unit in the sorting apparatus and/or about the contents of the source unit, or it can be criteria information that pertains to each of a plurality of samples that can be placed in the source unit. The criteria information, as described herein above, can be data that can be used to select entities such as samples, sample containers, tubes, material and/or compounds for sorting in the sorting apparatus. In a preferred embodiment, the criteria information can be one or more physical characteristics of one or more of the entities, such as a mass determination, a molecular structure, or a volume. A source code can embody, in coded and/or non-coded format, any of the source unit information or additional information as well. A source unit information label and/or a source code can be read manually and visually, and/or automatically read using an automated mechanism, such as a scanning device.

Optionally, in one embodiment, one or more labels reflecting destination unit information and/or one or more destination codes can be applied to or etched on one or more destination units. Destination unit information refers to any information that communicates various qualities pertaining to a destination unit, such as the status, function, condition, contents, and/or location of a destination unit within a sorting apparatus. A destination code can embody, in coded and/or non-coded format, any of the destination unit information or additional information as well. A destination unit information label and/or a destination code can be read manually and visually, and/or automatically read using an automated mechanism, such as a scanning device.

FIG. 2 schematically illustrates one embodiment that includes automatic mechanism 225 used to read, and/or scan, a label and/or a code. In a preferred embodiment automatic mechanism 225 is one or more optical system readers, one or more scanning mechanisms, one or more scanners, and/or other comparable reading mechanisms or devices. Automatic mechanism 225 reads, and/or scans, one or more source unit labels/codes, destination unit labels/codes, sample/sample container labels/codes, or any other type of label/code used in association with methods, systems and an apparatus of the present invention. Optionally, information obtained as a result of the reading and/or scanning is sent to a database associated with CPU 222. Labeling device control system unit 228 functionally controls labeling device 226. As shown, control system unit 228 is disposed on slideable platform 229, which is mounted on lower section 214B via slideable tracks 231

FIG. 3 illustrates one embodiment of lower section 214B of sorting apparatus 200 from a perspective view. As shown, lower section 214B is disposed below upper portion 214A (shown transparent) of platform 214. Although FIG. 3 schematically depicts a mechanical arrangement with components in particular locations, the present invention optionally includes other arrangements. FIG. 3 schematically illustrates stabilized balance 300 mounted on stabilizer 302. In a preferred embodiment, stabilizer 302 is granite stone, or any substance with comparable suitable dampening qualities. Stabilizer 302 enhances the accuracy of any measurements obtained using stabilized balance 300. As shown, stabilizer 302 is designed to hold multiple balances. Stabilized balance 300 and stabilizer 302 are coupled to a supporting framework (not shown) of sorting apparatus 200. Stabilized balance 300 can be accessed by automatic sorting mechanism 220 such that one or more samples, sample containers, material, or other entities that are engaged by automatic sorting mechanism 220 can be weighed on stabilized balance 300 in order to determine a mass of the entity.

The present invention is designed to optionally couple, and/or cooperatively operate, multiple compatible components in conjunction with sorting apparatus 200. For example, in one embodiment one or more fluid handling units (not shown) can be coupled to, or cooperatively operate in conjunction with, sorting apparatus 200. The fluid-handling unit can dispense or extract a specified amount of fluid to or from one or more samples and/or sample containers either before or after a sorting process has occurred.

The present invention contemplates the ability to optionally couple, and cooperatively operate, one or more workstations (not shown) in conjunction with sorting apparatus 200. For example, one or more samples/sample containers can be processed at a workstation according to specified instructions either before or after the sample/sample container is sorted or transferred. In one embodiment, a workstation can comprise one or more mass spectroscopy units (not shown) that can be used to evaluate one or more samples after the samples have been sorted and processed.

The present invention also contemplates the ability to cooperatively operate and/or couple one or more carrousels (not shown) to sorting apparatus 200. A carrousel can be a case, a container, a holding unit or mechanism that can contain one or more sample blocks, batches, or groups of material, samples, sample containers, tubes and/or other items. In one embodiment one or more carrousels are loaded with a plurality of source and/or destination units and used in conjunction with the sorting apparatus 200.

Referring now to FIGS. 2, 3, and 4 together, the present invention will be described in more detail. FIG. 4 illustrates one embodiment of upper section 214A of sorting apparatus 200 from a top view. Although FIG. 4 schematically depicts an arrangement with components in particular locations, the present invention optionally includes other arrangements. FIG. 4 schematically illustrates source unit 210 and destination unit 216. Although FIG. 4 depicts a square or rectangular shape for source unit 210 and for destination unit 216, the present invention optionally includes source units and destination units of varying shapes and sizes comprising any of a number of different footprints.

As shown, source unit 210 and destination unit 216 are designed to include a plurality of apertures. For example, source unit 210 and/or destination unit 216 are optionally designed as a tube holder comprising a plurality of apertures, a tube holder containing tubes, or a holder with other container types. In one embodiment, a plurality of samples or sample containers is located in one or more source units. Source unit 210 and/or destination unit 216 are optionally designed to comprise apertures that are configured to correspond to a spatial arrangement of one or more standard, and/or one or more non-standard formats.

A non-standard format refers to a spatial arrangement, configuration, form, positioning, structure, and/or shape that conforms to a custom design (e.g., other than a standard 96, 384 or 1536 well microtiter plate). A non-standard format is typically organized for a particular purpose. A standard format refers to a spatial arrangement, configuration, form, positioning, structure, and/or shape that conforms to a size and shape that is commonly encountered. In particular, a standard format refers to a standard design, size, shape, and configuration of a microtiter plate. Specifically, the size and shape of a standard 96 well, 384 well, and/or a 1536 well microtiter plate are contemplated; however, other standard designs, shapes and sizes are also compatible with the present invention. The present invention also contemplates any number of different standard and/or non-standard formats for source units, destination units, holding units, or other similar entities.

In one embodiment, one or more source units, and/or one or more destination units comprise one or more tube holders configured to receive one or more samples and/or sample containers. Optionally, the one or more tube holders are designed to include a plurality of apertures configured to correspond to various spatial arrangements, such as a spatial arrangement of wells in a standard 96 well microtiter plate format, or a standard 384 well microtiter plate format. In a preferred embodiment, a plurality of propylene tubes is located in the plurality of apertures of the source unit. Also, a plurality of samples can comprise, or can be contained within the plurality of tubes.

In another embodiment, one or more source units comprise one or more tube holders that have a plurality of apertures configured in a non-standard format. Source unit 210 having the non-standard format functions effectively in sorting apparatus 200 in conjunction with one or more destination units 216 that are designed to have apertures that are configured in either a standard or non-standard format.

In another embodiment, one or more source units 210 can be one or more tube holders that have apertures that are configured in a standard format. As such, source unit 210 can be used effectively in sorting apparatus 200 in conjunction with one or more destination units designed to have apertures that can be configured in a standard format, and/or a non-standard format. Essentially, the present invention contemplates any number of different scenarios wherein source units and/or destination units can comprise either the same footprint or different footprints in sorting apparatus 200. As further depicted in FIG. 4, optionally, source unit 210 and destination unit 216 are designed to be structurally and functionally equivalent. Thus, source unit 210 and destination unit 216 can be used interchangeably in sorting apparatus 200.

Referring to FIG. 4, one embodiment of automatic sorting mechanism 220 is shown. In accordance with the present invention, the automatic sorting mechanism can be any mechanical device, such as a robotic arm or a mechanical lever that can accurately engage/grasp and transfer material, samples/sample containers, as well as perform various other tasks. Any of a variety of traditional robotics can be employed to transfer samples, and/or sample containers, to and from source units, and/or destination units, between any holding unit, carrousel, and workstations. Such robotics can include robotic armatures, grasping components, conveyor systems (e.g., conveyor belts, etc.) or the like. Typically, robotic components are coupled to a control system that directs sample/sample container movement between source and destination units, workstations, and/or sample/sample container tracking within the system.

As shown in FIG. 4, automatic sorting mechanism 220 is depicted as centrally located, interposed between holding fixture 212 and loading fixture 218, with a perpendicular orientation to platform 214A to optionally access each of a plurality of samples in one or more source units, destination units, or holding stations. The present invention contemplates other orientations for automatic sorting mechanism 220 as well. Automatic sorting mechanism 220 is flexibly designed to perform three dimensional, x-y-z movements and optionally includes a plurality of mobile subunits 220A, 220B, 220C, 220D, and at least one engaging mechanism 230. Optionally, subunit 220A is flexibly designed to move vertically, horizontally, and/or rotationally. Subunit 220B moves in unison with the movement of subunit 220A, or optionally, simultaneously and/or in isolation, either vertically, and/or rotationally. Subunit 220C is flexibly designed to optionally move vertically, horizontally, and/or rotationally. Further, subunit 220D is flexibly designed to move vertically and/or rotationally. The present invention contemplates various other designs for automatic sorting mechanism 220 as well.

FIG. 5 schematically illustrates one embodiment of an engaging mechanism 230 of an automatic sorting mechanism from a detailed perspective view. Engaging mechanism 230 includes gripper component 232 that is optionally designed to include a plurality of gripping prongs 232A that radially open, and/or close in unison. In one embodiment, gripper component 232 includes four gripping prongs that open radially from a center point. In another embodiment, gripping prongs 232A maintain a substantially parallel orientation relative to each other to provide enhanced control and reliable contact with samples/sample containers. When automatic sorting mechanism 220 moves to access samples/sample containers, such as tubes, for selective transfer, automatic sorting mechanism rotates to a specified location, and/or moves vertically and/or horizontally depending upon the location of the sample/sample container. Gripping prongs 232A of gripper component 232 spread open radially from a center point to accept each sample/sample container, and gripping prongs 232A spirally closes down around each selected sample/sample container. A number of fiber optics 234 are strategically located on engaging mechanism 230 to optionally provide sensor capability. For example, position(s) of engaging mechanism 230 can be detected, and/or relative open and closed positions of gripper component 232.

Referring to FIG. 6, one embodiment of stabilized balance 300 from a partially transparent detailed perspective view is schematically illustrated. Stabilized balance 300 is operationally accessible from at least one opening 310 in protective cover 320. FIG. 6 depicts opening 310 disposed above balance weighing platform 340, however, various other designs are compatible with the present invention. Referring to FIGS. 4 and 6 together, platform opening 227 in upper portion 214A enables a sample/sample container to be placed on weighing platform 340 through platform opening 227. Automatic sorting mechanism 220 is designed to transfer one or more selected samples/sample containers from one or more source units, to weighing platform 340 of stabilized balance 300. As depicted in FIG. 4, balance display 360 provides a readout when samples/sample containers are weighed. In a preferred embodiment, the present invention includes operational coupling with a computer system as described herein or otherwise known in the art. As shown in FIGS. 2 and 3, for example, CPU 222 is operationally coupled to sorting apparatus 200. In accordance with the present invention, sample/sample container mass information is transmitted to CPU 222.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of sorting samples, the method comprising:
   a) providing at least one source unit having a first footprint and comprising a plurality of sample containers disposed in a first plurality of apertures, and at least one destination unit having a second footprint and comprising a second plurality of apertures, wherein the second footprint differs in size from the first footprint and/or the second plurality of apertures differs in number from the first plurality of apertures, and wherein either or both the first plurality of apertures and the second plurality of apertures are configured to correspond to a spatial arrangement of apertures of a standard 96 well microtiter plate or a standard 384-well microtiter plate;
   b) selectively transferring one or more of the plurality of sample containers to the destination unit using at least one automatic sorting mechanism, based upon one or more selected criteria, wherein the selected criteria comprise one or more sample descriptors and wherein samples comprising at least one common sample descriptor are grouped together in one or more destination units, and wherein the sample descriptors comprise a level of sample purity; and,
   c) repeating (a)-(b) at least once, thereby sorting the samples.

2. The method of claim 1, wherein the source unit comprises at least one tube holder configured in a non-standard format.

3. The method of claim 1, wherein the destination unit comprises a plurality of apertures configured in a non-standard format.

4. The method of claim 1, wherein the destination unit comprises a plurality of apertures configured to correspond to a spatial arrangement of wells of a standard 96 well microtiter plate format or a standard 384 well microtiter plate format.

5. The method of claim 1, wherein the source unit comprises at least one tube holder having the first plurality of apertures configured in a non-standard format and the destination unit comprises a tube holder having the second plurality of apertures configured to correspond to the spatial arrangement of a standard 96 well microtiter plate format or a standard 384 well microtiter plate format.

6. The method of claim 1, wherein the source unit comprises at least one tube holder having the first plurality of apertures configured to correspond to the spatial arrangement of a standard 96 well microtiter plate format or a standard 384 well microtiter plate format and the destination unit comprises a tube holder having the second plurality of apertures configured in a non-standard format.

7. The method of claim 1, wherein the source unit comprises at least one tube holder having the first plurality of apertures configured to correspond to the spatial arrangement of a standard 96 well microtiter plate format or a standard 384 well microtiter plate format and the destination unit comprises a tube holder having the second plurality of apertures configured to correspond to the spatial arrangement of a standard 96 well microtiter plate format or a standard 384 well microtiter plate format.

8. The method of claim 1, wherein the automatic sorting mechanism transfers the sample to one or more specific locations while simultaneously moving in a three-dimensional manner along x-y-z axes.

9. The method of claim 1, wherein the transferring further comprises placing the samples in one or more specified locations in at least one holding area.

10. The method of claim 1, wherein the selected criteria are stored in at least one database.

11. The method of claim 1, wherein the selected criteria comprise one or more physical characteristics of at least one sample in the sample containers.

12. The method of claim 1, wherein the selected criteria comprise at least one mass of at least one sample in the sample containers.

13. The method of claim 1, wherein the selected criteria comprise at least one structure of at least one sample in the sample containers.

14. The method of claim 1, wherein the selected criteria comprise at least one specific location of at least one of the sample containers in the at least one source unit.

15. The method of claim 1, wherein the automatic sorting mechanism comprises one or more carrousels and the method comprises mounting the at least one source unit on at least one of the carrousels.

16. The method of claim 1, wherein the automatic sorting mechanism comprises one or more carrousels and the method comprises mounting a plurality of source units on at least one of the carrousels.

17. The method of claim 1, wherein at least about 48 source units are provided and wherein the transferring comprises transferring one or more of the sample containers from the at least about 48 source units to at least about 6 destination units.

18. The method of claim 1, wherein the repeating comprises transferring one or more of the plurality of sample containers to at least one additional destination unit in (b), or providing at least one additional source unit in (a), or both, wherein the additional source unit comprises an additional plurality of sample containers.

19. The method of claim 1, further comprising: suspending a sample using the automatic sorting mechanism and processing the sample at one or more work stations as the sample is suspended.

20. The method of claim 1, further comprising: grouping the sample containers into at least one batch according to similar or identical criteria.

21. The method of claim 1, further comprising: arranging the sample containers into one or more discrete groups in the at least one destination unit.

22. The method of claim 1, further comprising: assigning at least one source code to the at least one source unit, which source code stores criteria information about each sample in the sample containers.

23. The method of claim 1, wherein the source unit comprises at least one tube holder, which tube holder comprises the first plurality of apertures configured to correspond to a spatial arrangement of wells of a standard 96 well microtiter plate format or a standard 384 well microtiter plate format.

24. The method of claim 23, wherein a plurality of tubes are located in the plurality of apertures.

25. The method of claim 1, wherein the plurality of sample containers comprise a plurality of tubes.

26. The method of claim 25, further comprising: i) weighing at least one sample or at least one tube to obtain a first mass, which first mass comprises a tare; ii) adding a material to the sample or the tube; iii) weighing the sample or the tube to obtain a second mass; and iv) deducting the tare from the second mass to obtain a mass of the material.

27. The method of claim 25, further comprising: grouping the sample containers into batches of up to about 96 tubes.

28. The method of claim 25, further comprising: grouping the sample containers into batches of up to about 384 tubes.

29. The method of claim 25, further comprising: importing data relating to the tubes.

30. The method of claim 29, wherein the imported data comprises tare weights of the tubes.

31. The method of claim 1, wherein each of the plurality of sample containers comprises an associated sample code, which associated sample code stores detailed information about each sample in the sample containers.

32. The method of claim 31, wherein the detailed information comprises criteria information, which criteria information is accessed when selectively transferring one or more of the plurality of sample containers.

33. The method of claim 31, wherein the detailed information comprises a final registry code of one or more of the plurality of sample containers, which final registry code stores sample processing information.

34. The method of claim 31, wherein each of the associated sample codes is read as the transferring occurs.

35. The method of claim 31, wherein the detailed information about each sample in the sample containers is stored in at least one database.

36. The method of claim 1, wherein the transferring comprises placing the sample containers in one or more specified locations in the at least one destination unit.

37. The method of claim 36, further comprising: conveying information about the specified locations to at least one database.

38. The method of claim 1, wherein the at least one destination unit is assigned at least one destination code.

39. The method of claim 38, further comprising: automatically reading the at least one destination code.

40. The method of claim 1, further comprising: labeling the source unit, and/or the destination unit, and/or at least one sample, or at least one container containing the sample, with source unit information, and/or destination unit information, and/or sample information, respectively, wherein the information is applied to the source unit, the destination unit, the sample, or to the container, with at least one labeling mechanism.

41. The method of claim 40, wherein updated information is applied after the sample has been processed at one or more workstations.

42. The method of claim 40, wherein the labeling mechanism comprises at least one laser etching unit.

43. The method of claim 40, wherein the labeling mechanism comprises at least one ink jet labeling unit.

44. The method of claim 40, wherein the source unit information comprises any information that concerns a location of a source unit, or a location of any material, container, sample, or sample container that is located in, and/or associated with, the source unit.

45. The method of claim 40, wherein the destination unit information comprises one or more destination codes, and/or information that communicates a status, a condition, contents, and/or a location, of a destination unit.

46. The method of claim 40, wherein the sample information comprises one or more of a sample code, a mass of the sample, a starting position of the sample, a destination position of the sample and/or a registration code of the sample, which registration code stores sample processing information.

47. The method of claim 46, further comprising: reading the sample information using at least one optical system reader.

48. The method of claim 46, further comprising: reading the sample information by manual/visual inspection.

49. A system for sorting samples, the system comprising:
at least one source unit having a first footprint and comprising a first plurality of apertures for a plurality of sample containers;
at least one destination unit having a second footprint and configured to receive one or more sample containers in a second plurality of apertures, wherein the second footprint differs in size from the first footprint and/or the second plurality of apertures differs in number from the first plurality of apertures, and wherein either or both the first plurality of apertures and the second plurality of apertures are configured to correspond to the spatial arrangement of a standard 96 well microtiter plate or a standard 384-well microtiter plate;
at least one sorting device comprising at least one automatic sorting mechanism, at least one holding fixture to receive the source unit, and at least one loading fixture to receive the destination unit; and,
at least one central processing unit which directs the repetitive transfer of one or more sample containers from the source unit to the destination unit based upon one or more selected criteria, wherein the selected criteria comprise one or more descriptors and wherein the central processing unit is configured to group samples, or sample containers, comprising at least one common descriptor together in one or more destination units, and wherein the common descriptor comprises a level of sample purity.

50. The system of claim 49, wherein the source unit comprises at least one tube holder configured in a non-standard format and the destination unit comprises at least one tube holder, which tube holder comprises the second plurality of apertures configured to correspond to the spatial arrangement of a standard 96 well microtiter plate format or a standard 384 well microtiter plate format.

51. The system of claim 49, wherein the source unit comprises at least one tube holder, which tube holder comprises the first plurality of apertures configured to correspond to the spatial arrangement of a standard 96 well microtiter plate format or a standard 384 well microtiter plate format and the destination unit comprises at least one tube holder configured in a non-standard format.

52. The system of claim 49, wherein the source unit comprises at least one tube holder, which tube holder comprises the first plurality of apertures configured to correspond to the spatial arrangement of a standard 96 well microtiter plate format or a standard 384 well microtiter plate format, and the destination unit comprises at least one tube holder, which tube holder comprises the second plurality of apertures configured to correspond to the spatial arrangement of a standard 96 well microtiter plate format or a standard 384 well microtiter plate format.

53. The system of claim 49, wherein the automatic sorting mechanism comprises one or more transferring units that move samples and/or the sample containers to one or more specific locations while simultaneously moving in a three-dimensional manner along x-y-z axes.

54. The system of claim 49, further comprising: one or more balances, which balances are configured to determine a mass of a sample, the sample container, or both.

55. The system of claim 49, further comprising: at least one fluid handling unit, which handling unit dispenses or extracts a specified amount of fluid liquid to or from one or more sample containers.

56. The system of claim 49, wherein the central processing unit is configured to import data relating to the sample containers.

57. The system of claim 56, wherein the imported data comprises tare weights of the sample containers.

58. The system of claim 49, wherein the source unit comprises at least one tube holder, which tube holder is configured to receive at least one of the sample containers.

59. The system of claim 58, wherein the tube holder comprises a plurality of apertures configured to correspond to a spatial arrangement of wells of a standard 96 microtiter plate well format or a standard 384 microtiter plate well format.

60. The system of claim 49, wherein a plurality of sample containers is located in the at least one source unit.

61. The system of claim 58, further comprising: at least one central database, which at least one central database is integrally associated with the at least one central processing unit and comprises data corresponding to the plurality of samples or sample containers, the at least one source unit, the at least one destination unit, and/or the at least one sorting device.

62. The system of claim 60, further comprising: at least one holding station, which holding station receives one or more samples or sample containers before, or after, the samples are transferred.

63. The system of claim 60, wherein the source unit is assigned at least one source code, which source code stores detailed information about the source unit, the plurality of samples or the sample containers.

64. The system of claim 63, further comprising: at least one automated mechanism for reading the at least one source code.

65. The system of claim 60, wherein each of the plurality of samples or sample containers comprise an associated sample code, which associated sample code stores detailed information about each of the plurality of samples or sample containers.

66. The system of claim 65, further comprising: at least one automated mechanism for reading each of the associated sample codes.

67. The system of claim 60, further comprising: at least one labeling mechanism configured to apply at least one label on at least one source unit, and/or at least one destination unit, and/or at least one sample or sample container.

68. The system of claim 67, further comprising at least one automatic mechanism for reading the label.

69. The system of claim 67, wherein the labeling mechanism comprises at least one inkjet labeling unit.

70. The system of claim 67, wherein the labeling mechanism comprises at least one laser etching unit.

71. The system of claim 49, further comprising: at least one work station, which work station processes one or more samples, or one or more sample containers according to specified instructions before the sample containers are transferred.

72. The system of claim 71, wherein the work station comprises at least one mass spectroscopy units.

73. The system of claim 49, wherein the at least one sorting device comprises one or more carrousels configured to receive at least one source unit or at least one destination unit.

74. The system of claim 73, wherein a plurality of source units are located in the carrousels.

75. The system of claim 49, wherein the at least one destination unit is assigned at least one destination code in the at least one central processing unit.

76. The system of claim 75, further comprising: at least one automated mechanism for reading the at least one destination code.

77. A method of sorting samples, the method comprising:
a) providing at least one source unit, which at least one source unit comprises a plurality of apertures, which apertures comprise a first footprint;
b) placing one or more samples in the at least one source unit, which one or more samples comprise at least one associated sample code, which at least one associated sample code stores detailed information about each of the one or more samples;
c) reading the at least one associated sample code of each of the samples as each of the samples is placed in the at least one source unit;
d) sending the detailed information about the plurality of samples to at least one database;
e) assigning at least one source code to the at least one source unit, which at least one source code stores the detailed information about the one or more samples placed in the at least one source unit;
f) loading the at least one source unit into at least one sorting device, which at least one sorting device comprises at least one automatic sorting mechanism;
g) scanning the source code of the at least one source unit;
h) designating the at least one source unit to at least one specific position under the at least one automatic sorting mechanism;
i) sending information about the at least one specific position to the at least one database;
j) loading at least one destination unit in the at least one sorting device, which at least one destination unit comprises at least one second footprint, different than the first footprint, and at least one destination code;
k) recording the at least one destination code as the at least one destination unit is loaded in the at least one sorting device;
l) accessing the at least one database;
m) selecting one or more of the samples in the at least one source unit for sorting;
n) transferring one or more of the samples from the at least one source unit into one or more specified locations in the at least one destination unit using the at least one automatic sorting mechanism;
o) conveying information about the one or more specified locations of the one or more samples to the at least one database; and
p) repeating (a)-(o) at least once.

* * * * *